(12) United States Patent
Lochmann et al.

(10) Patent No.: US 12,030,852 B2
(45) Date of Patent: Jul. 9, 2024

(54) METHOD FOR PRODUCING FATTY ALCOHOL ESTERS OF HYDROXYCARBOXYLIC ACIDS

(71) Applicant: IOI Oleo GmbH, Witten (DE)

(72) Inventors: Dirk Lochmann, Witten (DE); Sebastian Reyer, Witten (DE); Michael Stehr, Witten (DE)

(73) Assignee: IOI Oleo GmbH (DE)

( * ) Notice: Subject to any disclaimer, the term of this patent is extended or adjusted under 35 U.S.C. 154(b) by 0 days.

(21) Appl. No.: 17/378,967

(22) PCT Filed: Jan. 23, 2019

(86) PCT No.: PCT/EP2019/051546
§ 371 (c)(1),
(2) Date: Jul. 19, 2021

(87) PCT Pub. No.: WO2020/147982
PCT Pub. Date: Jul. 23, 2020

(65) Prior Publication Data
US 2023/0159430 A1  May 25, 2023

(30) Foreign Application Priority Data

Jan. 17, 2019  (WO) ................. PCT/EP2019/051125

(51) Int. Cl.
*C07C 67/02* (2006.01)
*C07C 67/03* (2006.01)
*C07C 67/08* (2006.01)
*C07C 69/675* (2006.01)
*C07C 69/732* (2006.01)
*C12P 7/62* (2022.01)

(52) U.S. Cl.
CPC ............ *C07C 69/675* (2013.01); *C07C 67/02* (2013.01); *C07C 67/03* (2013.01); *C07C 67/08* (2013.01); *C07C 69/732* (2013.01); *C12P 7/62* (2013.01); *C12Y 301/01* (2013.01)

(58) Field of Classification Search
CPC ......... C07C 67/02; C07C 67/03; C07C 67/08; C07C 69/675; C07C 69/732; C12P 7/62
See application file for complete search history.

(56) References Cited

U.S. PATENT DOCUMENTS 10,562,839 B2 * 2/2020 Verdin .................... A61P 35/00

FOREIGN PATENT DOCUMENTS

JP       2019178122 A  * 10/2019  ............. A61K 31/22

OTHER PUBLICATIONS

JP2019178122 (A), Sugimoto Masayuki et al., Human Normal Cell Activator, English translation, 12 pages (Year: 2019).*

* cited by examiner

*Primary Examiner* — Yate' K Cutliff
(74) *Attorney, Agent, or Firm* — Edward E. Sowers; Brannon Sowers & Cracraft PC

(57) ABSTRACT

The invention relates to a method for producing fatty alcohol esters of 3-hydroxybutyric acid and their acylated derivatives, as well as the products thus obtained and their use.

14 Claims, No Drawings

METHOD FOR PRODUCING FATTY ALCOHOL ESTERS OF HYDROXYCARBOXYLIC ACIDS

CROSS-REFERENCES TO RELATED APPLICATIONS

This application is a National Stage filing of International Application PCT/EP 2019/051541 filed Jan. 23, 2019, entitled "METHOD FOR PRODUCING FATTY ALCOHOL ESTERS OF HYDROXY CARBOXYLIC ACIDS", claiming priority to PCT/EP 2019/051125, filed Jan. 17, 2019. The subject application claims priority to PCT/EP 2019/051541 and PCT/EP 2019/051125, and incorporates all by reference herein, in their entirety.

BACKGROUND OF THE INVENTION

The present invention relates to the field of keto bodies and related metabolism and the therapy of related diseases.

Especially, the present invention relates to a method for producing fatty alcohol esters of 3-hydroxybutyric acid, as well as the reaction products thus obtainable or thus prepared (i.e. fatty alcohol esters of 3-hydroxybutyric acid) and their use, especially in pharmaceutical compositions, such as drugs (pharmaceuticals) or medicaments, or in food and/or food products, as well as their further applications or uses.

Also, the present invention relates to a method for producing fatty alcohol esters of acylated (e.g. acetylated) 3-hydroxybutyric acid (i.e. in other words, fatty alcohol esters of 3-acyloxybutyric acid (e.g. of 3-acetoxybutyric acid)) and the reaction products thus obtained or thus prepared (i.e. fatty alcohol esters of acylated 3-hydroxybutyric acid, i.e. fatty alcohol esters of 3-acyloxybutyric acid, e.g. of 3-acetoxybutyric acid) and their use, especially in pharmaceutical compositions, such as drugs (pharmaceuticals) or medicaments, or in food and/or food products, as well as their further applications or uses.

Furthermore, the present invention relates to pharmaceutical compositions, especially drugs (pharmaceuticals) or medicaments, comprising the reaction products (i.e. fatty alcohol esters of 3-hydroxybutyric acid and acylated derivates thereof) obtainable or produced according to the inventive method, as well as their applications or uses.

Finally, the present invention relates to food and/or food products, especially food supplements, functional foods, novel foods, food additives, food supplements, dietary foods, power snacks, appetite suppressants and strength and/or endurance sports supplements, which comprise the reaction products (i.e. fatty alcohol esters of 3-hydroxybutyric acid and acylated derivates thereof) obtainable or produced according to the inventive method, as well as their applications or uses.

In the human energy metabolism, glucose is the short-term available energy carrier, which is metabolized into energy in the mitochondria by releasing water and carbon dioxide. The glycogen stores of the liver are already emptied during the sleep period during the night. However, especially the human central nervous system (CNS) and the heart require a permanent energy supply.

The physiological alternative to glucose, which is mainly available to the central nervous system, are the so-called keto bodies (synonymously also called ketone bodies).

The term keto body is especially a collective term for three compounds, which are formed mainly in catabolic metabolic states (such as hunger, reduction diets or low-carbohydrate diets) and may lead to ketosis. The term keto bodies includes especially the three compounds acetoacetate (synonymously also referred to as acetacetate) and acetone as well as 3-hydroxybutyric acid (hereinafter also synonymously referred to as beta-hydroxybutyric acid or BHB or 3-BHB) or its salt (i.e. 3-hydroxybutyrate or beta-hydroxybutyrate), the latter being the most important of the three aforementioned compounds. 3-Hydroxybutyric acid or its salt occurs physiologically as the (R)-enantiomer, i.e. as (R)-3-hydroxybutyric acid (synonymously also called (3R)-3-hydroxybutyric acid to emphasize the center of chirality in the 3-position) or its salt.

These keto bodies are also provided physiologically in large amounts from lipids stored in the body by lipolysis during fasting or starvation and replace the energy source glucose almost completely.

The keto bodies are formed in the liver from acetyl coenzyme A (=acetyl-CoA), which originates from beta-oxidation; they represent a transportable form of the acetyl coenzyme A in the human body. However, in order to utilize the keto bodies, the brain and muscles must first adapt by expressing enzymes that are required to convert keto bodies back into acetyl coenzyme A. Especially in times of hunger, the keto bodies contribute a considerable amount to energy production. For example, after some time the brain is able to get by with only a third of the daily amount of glucose.

Physiologically, the keto bodies are synthesized from two molecules of activated acetic acid in the form of acetyl coenzyme A, the normal intermediate product of fatty acid degradation, which is extended using a further acetyl coenzyme A unit and the enzyme HMG-CoA-synthase to the intermediate product 3-hydroxy-3-methyl-glutaryl-CoA (HMG-CoA), wherein finally the HMG-CoA-lyase cleaves off the acetoacetate. These three steps take place exclusively in the mitochondria of the liver (lynen cycle), wherein 3-hydroxybutyrate is finally formed in the cytosol by the D-beta-hydroxybutyrate dehydrogenase. HMG-CoA is also an end product of the degradation of the amino acid leucine, while acetoacetate is formed during the degradation of the amino acids phenylalanine and tyrosine.

Spontaneous decarboxylation turns acetoacetate into acetone; it can occasionally be perceived in the breath of diabetics and dieters. It cannot be further used by the body. However, the proportion of acetone in the keto bodies is small.

Acetoacetate is thus reductively converted into the physiologically relevant form of 3-hydroxybutyric acid or 3-hydroxybutyrate, but can also decompose into the physiologically unusable acetone with the release of carbon dioxide, which is detectable and olfactory perceptible in severe ketosis, a ketoacidosis (e. g. in diabetes mellitus type 1 patients without insulin substitution), in the urine and in the exhaled air.

3-Hydroxybutyric acid is currently used and marketed in the weight training sector as a sodium, magnesium or calcium salt.

However, 3-hydroxybutyric acid is not known or only in very small quantities to humans in evolutionary terms, since plants do not produce 3-hydroxybutyric acid and 3-hydroxybutyric acid in the animal organism only occurs in dead emaciated animals in ketosis, so that 3-hydroxybutyric acid causes nausea when administered orally. 3-Hydroxybutyric acid in the form of free acid and its salts also taste very bitter and can cause severe vomiting and nausea.

Moreover, patients, especially newborns, but also adults cannot permanently tolerate large amounts of salts of 3-hydroxybutyric acid, as these compounds can have a kidney-damaging effect.

In addition, the plasma half-life of 3-hydroxybutyric acid and its salts is so short that even if several grams are taken, the ketosis lasts only for about three to four hours, i.e. patients cannot benefit continuously from a therapy with 3-hydroxybutyric acid or its salts, especially at night. In case of metabolic diseases this can lead to life-threatening situations.

Therefore, in the case of the therapy of such metabolic diseases, so-called medium-chain triglycerides, so-called MCTs, are currently used for ketogenic therapy, i.e. the metabolic conversion of caproic, caprylic and capric acid (i.e. of saturated linear $C_6$-, $C_8$- and $C_{10}$-fatty acids) from the corresponding triglycerides is intended.

Basically, however, from a pharmaceutical and clinical point of view, 3-hydroxybutyric acid is a more effective pharmaceutical-pharmacological target molecule, which, according to the prior art, could in principle be used for the therapy of a large number of diseases, but cannot be used due to its lack of physiological compatibility (e. g. in diseases in connection with a malfunction of the energy metabolism, especially keto-body metabolism, or neurodegenerative diseases such as dementia, Alzheimer's disease, Parkinson's disease, etc., lipometabolic diseases etc.).

The following table illustrates purely exemplary, but by no means limiting, potential therapy options or possible indications for the active ingredient 3-hydroxybutyric acid.

| Indication | Therapeutic effect |
| --- | --- |
| Traumatic brain injury | Under BHB the apoptosis and necrosis rate of nerve cells decreases. |
| Stroke | Under BHB the apoptosis and necrosis rate of nerve cells decreases. |
| Refeeding syndrome | In case of anorexia, discontinuation of enteral or parenteral nutrition and after long periods of hunger, the consumption of starch or glucose can lead to death (see also WHO scheme peanut paste). BHB can be used here as a therapeutic agent to achieve normal food intake more quickly. |
| Appetite suppressant | BHB suppresses the feeling of hunger in the central nervous system (CNS). |
| Epilepsy | Conventional ketogenic diet to significantly reduce the frequency of seizures has extremely poor patient tolerance, BHB offers an immediately effective alternative here. |
| Alzheimer's disease, dementia | Under BHB patients show better cognitive performance. BHB is also effective in the prevention of neurodegenerative diseases. |
| Disorders of fatty acid oxidation (e.g. electron transfer protein defect) | Compensation of a nutrient deficiency in case of defect in energy metabolism. |

Therefore, it is desirable from a pharmaceutical and clinical point of view to be able to find effective precursors or metabolites which physiologically allow direct or indirect access to 3-hydroxybutyric acid or its salts, especially in the physiological metabolism of the human or animal body.

Consequently, the prior art has not lacked attempts to find physiologically suitable precursors or metabolites for 3-hydroxybutyric acid or its salts. So far, however, no efficient compounds have been found in the prior art. Also, access to such compounds is not or not readily possible according to the prior art.

BRIEF SUMMARY OF THE INVENTION

The problem underlying the present invention is thus the provision of an efficient method for producing physiologically suitable or physiologically compatible precursors and/or metabolites of 3-hydroxybutyric acid (i.e. beta-hydroxybutyric acid or BHB or 3-BHB) or their salts.

Such method should especially make the respective BHB precursors and/or BHB metabolites accessible in an efficient way, especially in larger quantities and without significant amounts of toxic by-products.

In a completely surprising way, the applicant has now discovered that fatty alcohol esters of 3-hydroxybutyric acid (beta-hydroxybutyric acid, BHB or 3-BHB) and also fatty alcohol esters of acylated 3-hydroxybutyric acid (3-acyloxybutyric acid) represent an efficient and physiologically effective or physiologically compatible precursor and/or metabolite for the keto body 3-hydroxybutyric acid or its salts and has in this context been able to find or develop an efficient method for producing these compounds, which allows direct and effective, especially economic as well as industrially feasible access to these compounds.

To solve the problem described above, the present invention therefore proposes—according to a first aspect of the present invention—a method for producing fatty alcohol esters of 3-hydroxybutyric acid (beta-hydroxybutyric acid, BHB or 3-BHB).

Furthermore, the present invention relates—according to a second aspect of the present invention—to a reaction product obtainable according to the inventive method or a fatty alcohol ester of 3-hydroxybutyric acid (beta-hydroxybutyric acid, BHB or 3-BHB) as well as a reaction intermediate product obtainable according to the inventive method or a fatty alcohol ester of acylated 3-hydroxybutyric acid (3-acyloxybutyric acid).

Likewise, the present invention—according to a third aspect of the present invention—relates to a pharmaceutical composition, especially a drug (pharmaceutical) or medicament.

Furthermore, the present invention—according to a fourth aspect of the present invention—relates to an inventive reaction product or an inventive fatty alcohol ester of 3-hydroxybutyric acid (beta-hydroxybutyric acid, BHB or 3-BHB) as well as an inventive reaction intermediate product or an inventive fatty alcohol ester of acylated 3-hydroxybutyric acid (3-acyloxybutyric acid) in each case for the prophylactic and/or therapeutic treatment or in each case for use in the prophylactic and/or therapeutic treatment of diseases of the human or animal body.

Furthermore, the present invention—according to a fifth aspect of the present invention—relates to the use of an inventive reaction product or an inventive fatty alcohol ester of 3-hydroxybutyric acid (beta-hydroxybutyric acid, BHB or 3-BHB) as well as an inventive reaction intermediate product or an inventive fatty alcohol ester of acylated 3-hydroxybutyric acid (3-acyloxbutyric acid) in each case for the prophylactic and/or therapeutic treatment or in each case for producing a medicament for the prophylactic and/or therapeutic treatment of diseases of the human or animal body.

Furthermore, the present invention—according to a sixth aspect of the present invention—relates to the use of an inventive reaction product or an inventive fatty alcohol ester of 3-hydroxybutyric acid (beta-hydroxybutyric acid, BHB or 3-BHB) as well as an inventive reaction intermediate product or an inventive fatty alcohol ester of acylated 3-hydroxybutyric acid (3-acyloxybutyric acid) in each case for the prophylactic and/or therapeutic treatment or in each case for producing a medicament for the prophylactic and/or therapeutic treatment of or for the application for catabolic metabolic states.

Furthermore, the present invention—according to a seventh aspect of the present invention—relates to a food and/or food product; further, especially special and/or advantageous embodiments of the food and/or food product.

Finally, the present invention—according to an eighth aspect of the present invention—relates to the use of an inventive reaction product or an inventive fatty alcohol ester of 3-hydroxybutyric acid (beta-hydroxybutyric acid, BHB or 3-BHB) as well as an inventive reaction intermediate product or an inventive fatty alcohol ester of acylated 3-hydroxybutyric acid (3-aclyoxybutyric acid) in a food and/or a food product; further, especially special and/or advantageous embodiments of the use of the invention.

It goes without saying that following features, embodiments, advantages and the like, which are subsequently listed below only with regard to one aspect of the invention for the purpose of avoiding repetition, naturally also apply accordingly to the other aspects of the invention, without this requiring a separate mention.

Furthermore, it goes without saying that individual aspects and embodiments of the present invention are also considered disclosed in any combination with other aspects and embodiments of the present invention and, especially, any combination of features and embodiments, as it results from back references of all patent claims, is also considered extensively disclosed with regard to all resulting combination possibilities.

With respect to all relative or percentage weight-based data provided below, especially relative quantity or weight data, it should further be noted that within the scope of the present invention these are to be selected by the person skilled in the art such that they always add up to 100% or 100% by weight, respectively, including all components or ingredients, especially as defined below; however, this is self-evident for the person skilled in the art.

In addition, the skilled person may, if necessary, deviate from the following range specifications without leaving the scope of the present invention.

Additionally, it applies that all values or parameters or the like specified in the following can be determined or identified in principle with standardized or explicitly specified determination methods or otherwise with the determination or measurement methods that are otherwise familiar to a person skilled in the art.

Having stated this, the present invention will be described in more detail hereinafter:

DETAILED DESCRIPTION OF THE INVENTION

The subject-matter of the present invention—according to a first aspect of the present invention—is thus a method for producing fatty alcohol esters of 3-hydroxybutyric acid (beta-hydroxybutyric acid, BHB or 3-BHB), (A) wherein, according to a (first) synthesis route (A), at least one compound of the general formula (Ia)

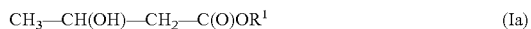  (Ia)

wherein, in the general formula (Ia), the radical $R^1$ represents hydrogen or $C_1$-$C_4$-alkyl, especially $C_1$-$C_4$-alkyl, preferably methyl or ethyl, more preferably ethyl, is reacted with at least one fatty alcohol (II) selected from $C_{10}$-$C_{30}$-fatty alcohols, especially $C_{10}$-$C_{24}$-fatty alcohols;

or else (B) wherein, according to a (second, alternative to (A)) synthesis route (B), at least one compound of the general formula (Ib)

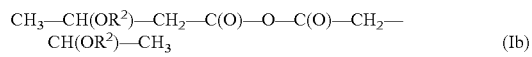  (Ib)

wherein, in the general formula (Ib), the radical $R^2$ represents an acyl group selected from —C(O)—$CH_3$ (acetyl group) or —C(O)—$C_2H_5$ (propionyl group), preferably —C(O)—$CH_3$ (acetyl group), is reacted with at least one fatty alcohol (II) selected from $C_{10}$-$C_{30}$-fatty alcohols, especially $C_{10}$-$C_{24}$-fatty alcohols, followed by hydrolysis of the acyl group;

so that, as a reaction product (III), in each case a $C_{10}$-$C_{30}$-fatty alcohol ester of 3-hydroxybutyric acid, especially a $C_{10}$-$C_{24}$-fatty alcohol ester of 3-hydroxybutyric acid, is obtained.

As stated above, the applicant has, quite surprisingly, discovered that the fatty alcohol esters of 3-hydroxybutyric acid (beta-hydroxybutyric acid, BHB or 3-BHB)—synonymously inter alia also referred to as "3-hydroxybutyric acid fatty alcohol ester" etc.—and furthermore also the reaction intermediate product according to synthesis route (B) before hydrolysis of the acyl group (i.e. fatty alcohol esters of acylated 3-hydroxybutyric acid or synonymously fatty alcohol esters of 3-acyloxybutyric acid) are each efficient, since physiologically compatible precursors and/or metabolites of 3-hydroxybutyric acid or their salts, which can also be used in larger quantities in pharmaceutical or clinical applications because they are physiologically compatible.

The above-mentioned fatty alcohol esters of 3-hydroxybutyric acid or of acylated 3-hydroxybutyric acid, which are accessible for the first time in an efficient manner through the production method according to the invention, represent a physiologically and pharmacologically relevant alternative to free 3-hydroxybutyric acid or its salts.

The production of fatty alcohol esters of 3-hydroxybutyric acid or of acylated 3-hydroxybutyric acid by means of conventional organic synthesis is complex and costly, since 3-hydroxybutyric acid has an increased tendency to polymerize and to undergo other undesirable side reactions (e. g. dehydration, decomposition, etc.). Within the scope of the present invention, it was possible for the first time to provide an efficiently working production method with which fatty alcohol esters of 3-hydroxybutyric acid or of acylated 3-hydroxybutyric acid can be produced without undesired side reactions, especially in a single step.

The inventive method thus makes it possible for the first time to provide non-toxic fatty alcohol esters of 3-hydroxybutyric acid or of acylated 3-hydroxybutyric acid from known, commercially available and above all physiologically harmless components or educts (starting compounds). The resulting fatty alcohol esters of 3-hydroxybutyric acid or of acylated 3-hydroxybutyric acid can be broken down physiologically, especially in the stomach and/or bowl, and release or generate the target molecule "3-hydroxybutyric acid" or its salts as active ingredient or active component.

In addition, the aforementioned fatty alcohol esters of 3-hydroxybutyric acid or of acylated 3-hydroxybutyric acid also comprise an acceptable taste to ensure compatibility even when administered orally in larger quantities over a longer period of time (e. g. administration of 50 g daily dose or more).

Similarly, the production method according to the invention makes it possible to provide the fatty alcohol esters of 3-hydroxybutyric acid or of acylated 3-hydroxybutyric acid free from toxic impurities.

In addition, with appropriate starting materials, the method can also be carried out enantioselectively. For example, according to the invention, the production method allows the biologically relevant form, i.e. the (R)-enantiomer, to be enriched, especially by enzyme catalysis, as not to burden the renal system of patients when administered orally (i.e. elimination via the kidneys). In principle, however, it is also possible, and under certain conditions may be useful, to enrich the (S)-enantiomer.

In addition, the production method according to the invention, including optional further processing or purification steps, can be operated economically and can also be implemented on a large scale.

Especially, the inventive production method uses commercially available or easily accessible starting compounds and furthermore allows a relatively simple process management even in case of large-scale implementation.

In contrast to conventional prior art production methods, the production method according to the invention does not use complex starting materials and uses only a single step. Nevertheless, excellent yields are achieved in accordance with the invention, wherein the formation of by-products is minimized or avoided.

In addition, the inventive method is simple and economical. Especially, the method according to the invention is usually carried out in the absence of solvents and/or without any solvent (i.e. as a reaction in mass or as a reaction in substance or as a so-called bulk reaction); consequently, the reaction products obtained are not contaminated with solvent and no solvent has to be removed and disposed of or recycled in a costly and energy-intensive manner after the method or reaction has been carried out. Furthermore, no toxic by-products are formed.

If desired, the crude reaction product resulting from the production process according to the invention can be purified in a simple manner and without further ado, especially by known methods, especially by removing any remaining starting compounds and/or any by-products present (e.g. by distillation and/or chromatography etc.).

Synthesis Route (A)

The following comments refer to synthesis route (A) of the inventive method.

According to a particular embodiment of the present invention, according to synthesis route (A), the compound of the general formula (Ia) may be used either in racemic form or in the form of the (R)-enantiomer. The (R)-configuration refers to the chiral carbon atom in 3-position of the compound of the general formula (Ia).

According to the invention, it is preferred if according to synthesis route (A), in the general formula (I), the radical $R^1$ represents ethyl.

In other words, it is preferred according to the invention that according to synthesis route (A), as compound of the general formula (Ia), 3-hydroxybutyric acid ethyl ester (ethyl 3-hydroxybutyrate) of the formula $CH_3$—$CH(OH)$—$CH_2$—$C(O)OC_2H_5$ is used.

This enables particularly efficient process control and high yields with minimized or suppressed by-product formation. In addition, the 3-hydroxybutyric acid ethyl ester is also commercially available in large quantities and can also be converted more efficiently than the free acid (i.e. 3-hydroxybutyric acid). Especially, the 3-hydroxybutyric acid ethyl ester can be obtained on a large scale as a starting compound, e. g. by Claisen condensation of ethyl acetate.

Especially, in the inventive method, according to synthesis route (A), the reaction is carried out in the absence of solvents and/or without any solvent. This means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

According to a particular embodiment of the present invention, according to synthesis route (A), the reaction can be carried out in the presence of a catalyst, especially an enzyme and/or a metal-containing and/or metal-based, acidic or basic catalyst, preferentially in the presence of an enzyme. In this particular embodiment, it is preferred that the catalyst is recycled after the reaction As mentioned hereinabove, according to the invention, the reaction can be carried out in the presence of an enzyme as catalyst.

In this context, the enzyme can especially be selected from synthetases (ligases), catalases, esterases, lipases and combinations thereof. According to the invention, synthetases (synonymously ligases) are especially enzymes from the class of ligases; ligases are enzymes which catalyze the linking of two or more molecules by a covalent bond. Catalases in the sense of the present invention are especially enzymes which are capable of converting hydrogen peroxide to oxygen and water. The term esterases refers in particular to enzymes which are capable of hydrolytically splitting esters into alcohol and acid (saponification); these are thus especially hydrolases, wherein fat splitting esterases are also called lipases. Lipases in the sense of the present invention are especially enzymes which are capable of splitting free fatty acids from lipids such as glycerides (lipolysis).

Within the scope of the present invention, according to synthesis route (A), the enzyme used as catalyst can especially be derived from *Candida antarctica, Mucor miehei (Rhizomucor miehei), Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially from *Candida antarctica, Mucor miehei (Rhizomucor miehei)* and *Thermomyces lanuginosus*.

According to a specific embodiment, according to synthesis route (A), the enzyme can be used in immobilized form, immobilized on a carrier, preferentially on a polymeric carrier, preferably on a polymeric organic carrier, more preferably with hydrophobic properties, even more preferably on a poly(meth)acrylic resin-based carrier.

As explained hereinabove with respect to the use of a catalyst in general, when an enzyme is used as a catalyst, according to synthesis route (A), it is preferred to recycle the enzyme after the reaction.

According to this particular embodiment of the inventive method, according to synthesis route (A), respective commercially available enzymes of the aforementioned definition can be used as the enzyme described hereinabove (e.g. CALB lipase on polymer support derived from *Candida antarctica*, e.g. Novozymm 435 from Sigma-Aldrich or Merck or Lipozym® 435 from Strem Chemicals, Inc.).

If the reaction, according to synthesis route (A), is carried out in the presence of an enzyme as a catalyst within the framework of the inventive production method, it is preferred if the reaction is carried out at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

In case of using an enzyme as a catalyst, according to synthesis route (A), the amount of the enzyme used can vary within a wide range. Especially, the enzyme can be used in amounts, based on the total amount of the starting compounds (Ia) and (II), in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight. Nevertheless, it may be necessary to deviate from the above-mentioned amounts in individual cases or for specific applications without leaving the scope of the present invention.

If, according to a particular embodiment of the present invention, according to synthesis route (A), the reaction is carried out in the presence of an enzyme as a catalyst, the applied pressure range may also vary within a wide range. Especially, if the reaction is carried out in the presence of an enzyme as a catalyst, the reaction can be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to an alternative embodiment of the present invention, the reaction according to synthesis route (A) may also be carried out in the presence of a metal-containing and/or metal-based, acidic or basic catalyst.

According to this alternative embodiment of the present invention, according to synthesis route (A), according to which the reaction is carried out in the presence of a metal-containing and/or metal-based, acidic or basic catalyst, the catalyst can especially be selected from (i) basic catalysts, especially alkali or alkaline earth hydroxides and alkali or alkaline earth alcoholates, such as NaOH, KOH, LiOH, Ca(OH)$_2$, NaOMe, KOMe and Na(OBu-tert.), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

According to this embodiment, especially an alkali or alkaline earth alcoholate can be used as a catalyst according to synthesis route (A).

Especially, also according to this embodiment, according to synthesis route (A), it is preferred if the catalyst based on the metal-containing and/or metal-based, acidic or basic catalyst is recycled after the reaction.

If, according to the particular embodiment of the present invention, the reaction, according to synthesis route (A), is carried out in the presence of a metal-containing and/or metal-based, acidic or basic catalyst, the temperatures can be varied within a wide range. Especially, the reaction can be carried out in the presence of a metal-containing and/or metal-based, acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Furthermore, also according to this embodiment, according to synthesis route (A), the catalyst (i.e. the metal-containing and/or metal-based, acidic or basic catalyst) can also be varied within wide quantity ranges: For example, the catalyst based on a metal-containing and/or metal-based, acidic or basic catalyst can be used in amounts, based on the total amount of the starting compounds (Ia) and (II), in the range of from 0.01 to 30% by weight, especially in the range of from 0.05 to 15% by weight, preferentially in the range of from 0.1 to 15% by weight, preferably in the range of from 0.2 to 10% by weight. Nevertheless, it is possible to deviate from the above-mentioned amounts for specific applications or individual cases without leaving the scope of the present invention.

If, according to this particular embodiment of the present invention, according to synthesis route (A), the reaction is carried out in the presence of a metal-containing and/or metal-based, acidic or basic catalyst, the pressure range can equally vary within a wide range: Especially, the reaction can be carried out in the presence of a metal-containing and/or metal-based, acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

As far as the quantity of starting materials or starting compounds, according to synthesis route (A), is concerned, this can also be varied within a wide range.

Taking into account process economy and optimization of the course of the method, especially with regard to the minimization of by-products, it is advantageous, according to synthesis route (A), if the compound of the general formula (Ia), based on the hydroxyl groups of the fatty alcohol (II) is used in molar amounts in a range of from equimolar amount up to a molar excess of 200 mol-%, especially in a range of from equimolar amount up to a molar excess of 150 mol-%, preferentially in a range of from equimolar amount up to a molar excess of 100 mol-%.

Similarly, taking into account process economy and optimization of the course of the method, especially with regard to minimizing by-products, according to synthesis route (A), it is advantageous if the compound of the general formula (Ia) and the fatty alcohol (II) are used in a molar ratio of compound of the general formula (I)/polyol (II) in a range of from 1:1 to 10:1, especially in a range of from 2:1 to 8:1, preferably in a range of from 3:1 to 6:1.

According to a preferred embodiment of the inventive method, according to synthesis route (A), it is preferred that according to synthesis route (A), at least one compound of the general formula (Ia')

$$CH_3-CH(OH)-CH_2-C(O)OC_2H_5 \quad (Ia')$$

is reacted with at least one fatty alcohol (II) selected from $C_{10}$-$C_{30}$-fatty alcohols, especially $C_{10}$-$C_{24}$-fatty alcohols; so that, as a reaction product (III), a $C_{10}$-$C_{30}$-fatty alcohol ester of 3-hydroxybutyric acid, especially a $C_{10}$-$C_{24}$-fatty alcohol ester of 3-hydroxybutyric acid, is obtained.

Within the scope of the inventive method, according to synthesis route (A), during the reaction, the compound according to the general formula (IVa)

$$R^1-OH \quad (IVa)$$

is formed simultaneously, wherein, in general formula (IVa), the radical $R^1$ represents hydrogen or $C_1$-$C_4$-alkyl, especially $C_1$-$C_4$-alkyl, preferably methyl or ethyl, more preferably ethyl. Especially, it is preferred in this context, if according to synthesis route (A), the compound according to the general formula (IVa) is withdrawn from the reaction, especially continuously withdrawn, especially by means of preferentially continuous removal by distillation.

Synthesis Route (B)

The following comments refer to synthesis route (B) of the inventive method.

According to a particular embodiment of the present invention, according to synthesis route (B), the compound of the general formula (Ib) may be used in racemic form or in the form of the (R)-enantiomer. The (R)-configuration refers to the two chiral carbon atoms of the compound of general formula (Ib), i.e. the carbon atoms marked "*" below in the compound of general formula (Ib), each of these chiral centers correspond to the respective C-atom in the 3-position of 3-hydroxybutyric acid:

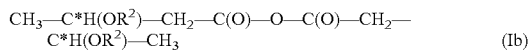

(Ib)

Especially, according to the inventive method, it is preferred when, according to synthesis route (B), in the general formula (Ib), the radical $R^2$ represents a group —C(O)—CH$_3$ (acetyl group) and/or when, according to synthesis route (B), as a compound of the general formula (Ib), the compound of formula CH$_3$—CH(OAc)—CH$_2$—C(O)—O—C(O)—CH$_2$—CH(OAc)—CH$_3$, wherein the radical Ac represents an acetyl group, is used.

Especially, in the inventive method, according to synthesis route (B), the reaction is carried out in the absence of solvents and/or without any solvent. This means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

According to a particular embodiment of the inventive method, according to synthesis route (B), the reaction may especially be carried out autocatalytically or in the presence of a catalyst, especially a mineral acid. However, preferably the reaction according to synthesis route (B) is carried our autocatalytically.

Provided that the reaction according to synthesis route (B) is carried out in the presence of a catalyst, it is preferred when, according to synthesis route (B), the reaction is carried out in the presence of a mineral acid. Especially, according to this embodiment, according to synthesis route (B), the catalyst and/or the mineral acid may be selected from sulfuric acids, hydrohalic acids, phosphoric acids and combinations thereof.

Within the scope of the inventive production method according to synthesis route (B), it is preferred if, according to synthesis route (B), the reaction is carried out at temperatures in the range of from 20° C. to 150° C., especially in the range of from 50° C. to 140° C., preferentially in the range of from 60° C. to 130° C., more preferably in the range of from 70° C. to 125° C., even more preferably in the range of from 75° C. to 110° C.

Furthermore, within the scope of the inventive production method, it is preferred if, according to synthesis route (B), the reaction is carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

As far as the quantity of starting materials or starting compounds is concerned, this can also be varied within a wide range according to synthesis route (B).

Taking into account process economy and optimization of the course of the method, especially with regard to the minimization of by-products, it is advantageous if, according to synthesis route (B), the compound of the general formula (Ib), based on the hydroxyl groups of the fatty alcohol (II), is used in molar amounts in a range of from equimolar amount up to a molar excess of 200 mol-%, especially in a range of from equimolar amount up to a molar excess of 150 mol-%, preferentially in a range of from equimolar amount up to a molar excess of 100 mol-%.

Similarly, taking into account process economy and optimization of the course of the method, especially with regard to minimizing by-products, it is advantageous if, according to synthesis route (B), the compound of general formula (Ib) and the fatty alcohol (II) are used in a molar ratio of compound of the general formula (Ib)/fatty alcohol (II) in a range of from 1:1 to 10:1, particularly in a range of from 2:1 to 8:1, preferentially in a range of from 3:1 to 6:1.

According to a preferred embodiment of the inventive method according to synthesis route (B), it is preferred that, according to synthesis route (B), at least one compound of the general formula (Ib')

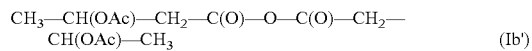

(Ib')

wherein, in the general formula (Ib'), the radical Ac represents an acetyl group, is reacted with at least one fatty alcohol (II) selected from $C_{10}$-$C_{30}$-fatty alcohols, especially $C_{10}$-$C_{24}$-fatty alcohols, followed by hydrolysis of the acyl group;

so that, as a reaction product (III), a $C_{10}$-$C_{30}$-fatty alcohol ester of 3-hydroxybutyric acid, especially a $C_{10}$-$C_{24}$-fatty alcohol ester of 3 hydroxybutyric acid, is obtained.

Within the scope of the inventive method, according to synthesis route (B), during the reaction, the compound according to the general formula (IVb)

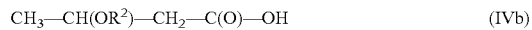

(IVb)

is formed simultaneously, wherein, in the general formula (IVb), the radical $R^2$ represents an acyl group selected from —C(O)—CH$_3$ (acetyl group) or —C(O)—C$_2$H$_5$ (propionyl group), preferably —C(O)—CH$_3$ (acetyl group). Especially, it is preferred in this context if, according to synthesis route (B), the compound according to the general formula (IVb) is withdrawn after the reaction has taken place, especially by means of removal by distillation.

Within the scope of the inventive method, according to synthesis route (B), the reaction of the at least one compound of the general formula (Ib), as defined hereinabove, with the at least one fatty alcohol (II), as defined hereinabove, is followed hydrolysis of the acyl group formed during this reaction; for, this reaction also leads to the hydroxyl function located in the 3-position of 3-hydroxybutyric acid being acylated, especially acetylated or propionylated (i.e. replacement of the hydrogen atom of the hydroxyl function located in the 3-position of 3-hydroxybutyric acid by an acyl group, especially by an acetyl group —C(O)—CH$_3$ or by a propionyl group —C(O)—C$_2$H$_5$). The hydrolysis of the acyl group carried out according to synthesis route (B) then finally leads to reaction product (III) free of acyl groups. For this purpose, according to the invention, according to synthesis route (B), the reaction of the at least one compound of the general formula (Ib), as defined hereinabove, with the at least one fatty alcohol (II), as defined hereinabove, is followed by a selective or partial hydrolysis of the acyl groups present in the reaction products (=reaction intermediates) after the reaction is carried out. Thus, reaction products (III) according to the following definition can be obtained, wherein the acyl group is replaced by a hydrogen atom during the hydrolysis and which consequently contain a free hydroxyl function (namely in the position of the reaction product (III) which goes back to the 3-position of the 3-hydroxybutyric acid part in the reaction product (III)).

Especially, it is preferred if, according to synthesis route (B), the hydrolysis of the acyl group, especially the acetyl group, is carried out in the presence of a catalyst, preferably an enzyme. This ensures a selective or partial hydrolysis of the acyl group, especially under mild and economical conditions, preferentially avoiding the formation of by-products.

Especially, it may be preferred if, according to synthesis route (B), the enzyme used for the hydrolysis of the acyl group, especially the acetyl group, may be selected from synthetases (ligases), catalases, esterases, lipases and combinations thereof. According to the invention, synthetases (synonymously ligases) are especially enzymes from the class of ligases; ligases are enzymes which catalyze the linking of two or more molecules by a covalent bond. Catalases in the sense of the present invention are especially enzymes which are capable of converting hydrogen peroxide to oxygen and water. The term esterases refers in particular to enzymes which are capable of hydrolytically splitting esters into alcohol and acid (saponification); these are thus especially hydrolases, wherein fat splitting esterases are also called lipases. Lipases in the sense of the present invention are especially enzymes which are capable of splitting free fatty acids from lipids such as glycerides (lipolysis).

Especially, according to synthesis route (B), the enzyme used for the hydrolysis of the acyl group, especially the acetyl group, may be derived from *Candida antarctica, Mucor miehei (Rhizomucor miehei), Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially of *Candida antarctica, Mucor miehei (Rhizomucor miehei)* and *Thermomyces lanuginosus*.

Especially, according to synthesis route (B), the enzyme used for the hydrolysis of the acyl group, especially of the acetyl group, may be used in immobilized form, especially immobilized on a carrier, preferentially on a polymeric carrier, preferably on a polymeric organic carrier, more preferably with hydrophobic properties, even more preferably on a poly(meth)acrylic resin-based carrier.

Especially, according to synthesis route (B), the enzyme used for the hydrolysis of the acyl group, especially the acetyl group, may be used in amounts, based on the total amount of the compound to be hydrolyzed, in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight.

According to this particular embodiment, it is preferred if, according to synthesis route (B), the enzyme used for the hydrolysis of the acyl group, especially the acetyl group, is recycled after the hydrolysis.

According to synthesis route (B), the hydrolysis of the acyl group, especially of the acetyl group, may be carried out at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

According to synthesis route (B), the hydrolysis of the acyl group, especially of the acetyl group, may be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

Typically, according to synthesis route (B), the hydrolysis of the acyl group, especially of the acetyl group, is carried out in the presence of water.

According to this particular embodiment of the inventive method, according to synthesis route (B), commercially available enzymes of the aforementioned definition can be used as the enzyme described hereinabove (e.g. CALB lipase on polymer support derived from *Candida antarctica*, e.g. Novozym® 435 from Sigma-Aldrich or Merck or Lipozym® 435 from Strem Chemicals, Inc.).

As described hereinabove, according to synthesis route (B), the compound of the general formula (Ib), as defined hereinabove, is used as a reactant. The compound of general formula (Ib), as defined hereinabove, is readily or easily accessible.

As far as the compound of general formula (Ib), as defined hereinabove, used in the inventive method according to synthesis route (B) is concerned, it is obtainable and/or obtained by reacting a carboxylic acid anhydride of general formula (V)

$$R^2\text{—}O\text{—}R^2 \qquad (V)$$

wherein the radical $R^2$ has the meaning defined hereinabove, especially acetic anhydride or propionic anhydride, preferentially acetic anhydride, with 3-hydroxybutyric acid.

Especially, the reaction of carboxylic acid anhydride of the general formula (V) with 3-hydroxybutyric acid can take place according to the reaction equation

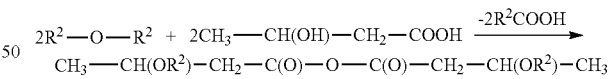

wherein the radical $R^2$ has the meaning defined hereinabove.

According to a particular embodiment, the reaction of acetic anhydride with 3-hydroxybutyric acid can take place according to the reaction equation

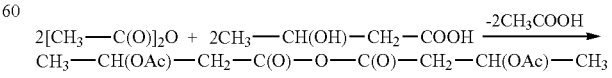

wherein the radical Ac represents an acetyl group.

The temperatures of the reaction of carboxylic acid anhydride of the general formula (V), as defined hereinabove, with 3-hydroxybutyric acid can vary within wide ranges. Especially, the reaction of carboxylic acid anhydride of general formula (V), as defined hereinabove, with 3-hydroxybutyric acid may be carried out at temperatures in the range of from 60 to 150° C., especially in the range of from 70 to 120° C., preferentially in the range of from 80 to 100° C.

The pressure of the reaction of carboxylic acid anhydride of the general formula (V), as defined hereinabove, with 3-hydroxybutyric acid can equally vary within wide ranges.

Especially, the reaction of carboxylic acid anhydride of the general formula (V), as defined hereinabove, with 3-hydroxybutyric acid may be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to a particular embodiment of the inventive method according to synthesis route (B), the present invention relates to a method for producing fatty alcohol esters of 3-hydroxybutyric acid (beta-hydroxybutyric acid, BHB or 3-BHB) as described hereinabove, wherein, according to synthesis route (B),
(a) in a first method step (a), a carboxylic acid anhydride of the previously defined general formula (V)

$$R^2\text{—}O\text{—}R^2 \quad (V)$$

wherein $R^2$ has the meaning defined hereinabove, especially acetic anhydride or propionic anhydride, preferably acetic anhydride, is reacted with 3-hydroxybutyric acid to obtain a compound of general formula (Ib), as defined hereinabove; and subsequently (b) in a second method step (b), the compound of general formula (Ib), as defined hereinabove, thus obtained is reacted with at least one fatty alcohol (II) selected from $C_{10}$-$C_{30}$-fatty alcohols, especially $C_{10}$-$C_{24}$-fatty alcohols, as defined hereinabove; and subsequently (c) in a third method step (c), the hydrolysis of the acyl group takes place, so that, as a reaction product (III), a $C_{10}$-$C_{30}$-fatty alcohol ester of 3-hydroxybutyric acid, especially a $C_{10}$-$C_{24}$-fatty alcohol ester of 3-hydroxybutyric acid, is obtained.

As already stated hereinabove in connection with synthesis route (B), the reaction carried out according to synthesis route (B), of the at least one compound of the general formula (Ib), as defined hereinabove with the at least one fatty alcohol (II), as defined hereinabove, also leads to the acylation, especially acetylation or propionylation, of the hydroxyl function located in the 3-position of the 3-hydroxybutyric acid (i.e. replacement of the hydrogen atom of the hydroxyl function located in the 3-position of 3-hydroxybutyric acid by an acyl group, especially by an acetyl group —C(O)—CH$_3$ or by a propionyl group —C(O)—C$_2$H$_5$). This reaction product (=reaction intermediate (IIIa)) obtained during the reaction of the at least one compound of general formula (Ib), as defined hereinabove, with the at least one fatty alcohol (II), as defined hereinabove, can be separated or isolated without being followed by hydrolysis of the acyl group.

Since, as already mentioned hereinabove, the applicant has surprisingly found out that the reaction intermediates (IIIa) formed according to synthesis route (B) before hydrolysis of the acyl group (i.e. fatty alcohol esters of the acylated 3-hydroxybutyric acid or synonymously fatty alcohol esters of 3-acyloxybutyric acid) are efficient, physiologically compatible precursors and/or metabolites of 3-hydroxybutyric acid or its salts, which can also be used pharmaceutically or clinically in larger quantities, since they are physiologically compatible; these reaction intermediates therefore equally represent a physiologically and pharmacologically relevant alternative to the free 3-hydroxybutyric acid or salts thereof.

According to a particular embodiment according to synthesis route (B), prior to hydrolysis of the acyl group, especially of the acetyl group, as a reaction intermediate (IIIa), a $C_{10}$-$C_{30}$-fatty alcohol ester of acylated 3-hydroxybutyric acid (3-acyloxybutyric acid), especially a $C_{10}$-$C_{24}$-fatty alcohol ester of acylated 3-hydroxybutyric acid (3-acyloxybutyric acid), preferentially a linear or branched, saturated or mono- or polyunsaturated aliphatic $C_{10}$-$C_{30}$-fatty alcohol ester of acylated 3-hydroxybutyric acid (3-acyloxybutyric acid), preferably a linear or branched, saturated or mono- or polyunsaturated aliphatic $C_{10}$-$C_{24}$-fatty alcohol ester of acylated 3-hydroxybutyric acid (3-acyloxybutyric acid), can be obtained.

According to a further particular embodiment, according to synthesis route (B), prior to hydrolysis of the acyl group, especially of the acetyl group, as a reaction intermediate (IIIa), a carboxylic acid ester of acylated 3-hydroxybutyric acid (3-acyloxybutyric acid) derived from a $C_{10}$-$C_{30}$-fatty alcohol, especially a carboxylic acid ester of acylated 3-hydroxybutyric acid (3-acyloxybutyric acid) derived from a $C_{10}$-$C_{24}$-fatty alcohol, preferentially a carboxylic acid ester derived from a linear or branched $C_{10}$-$C_{24}$-fatty alcohol, preferably a carboxylic ester of acylated 3-hydroxybutyric acid (3-acyloxybutyric acid) derived from a linear or branched, saturated or mono- or polyunsaturated, aliphatic monohydric and preferably primary $C_{10}$-$C_{30}$-fatty alcohol, preferably a carboxylic ester of acylated 3-hydroxybutyric acid (3-acyloxybutyric acid) derived from a linear or branched, saturated or mono- or polyunsaturated, aliphatic monohydric and preferably primary $C_{10}$-$C_{24}$-fatty alcohol, can be obtained.

Especially, in this context, the $C_{10}$-$C_{30}$-fatty alcohol, especially $C_{10}$-$C_{24}$-fatty alcohol, may be selected from the group of 1-decanol, 1-dodecanol (lauryl alcohol), 1-tetradecanol (myristyl alcohol), 1-hexadecanol (cetyl alcohol), 1-heptadecanol (margaryl alcohol), 1-octadecanol (stearyl alcohol), 1-eicosanol (arachidyl alcohol), 1-docosanol (behenyl alcohol), 1-tetracosanol (ligoceryl alcohol), 1-hexacosanol (ceryl alcohol), 1-octacosanol (montanyl alcohol), 1-tricontanol (melissyl alcohol), cis-9-hexadecen-1-ol (palmitoleyl alcohol), cis-9-octadecen-1-ol (oleyl alcohol), trans-9-octadecen-1-ol (elaidyl alcohol), cis-11-octadecen-1-ol, cis,cis-9,12-octadecadien-1-ol (linoleyl alcohol), 6,9,12-octadecatrien-1-ol (γ-linolenyl alcohol), and combinations thereof, preferably cis-9-octadecen-1-ol (oleyl alcohol).

According to the invention, it is preferred in this context that the acylated 3-hydroxybutyric acid (3-acyloxybutyric acid) is an acetylated 3-hydroxybutyric acid (3-acetoxybutyric acid).

According to yet another particular embodiment according to synthesis route (B), prior to hydrolysis of the acyl group, especially the acetyl group, as a reaction intermediate (IIIa), a carboxylic acid ester of a acylated 3-hydroxybutyric acid (3-acyloxybutyric acid), derived from a linear, saturated or mono- or polyunsaturated aliphatic, monohydric primary $C_{10}$-$C_{24}$-fatty alcohol, can be obtained.

Finally, according to a likewise further particular embodiment according to synthesis route (B), prior to hydrolysis of the acyl group, especially the acetyl group, as reaction intermediate (IIIa), a fatty alcohol ester of acylated 3-hydroxybutyric acid (3-acyloxybutyric acid) of the general formula (IIIa)

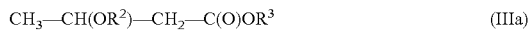

$$CH_3-CH(OR^2)-CH_2-C(O)OR^3 \quad \text{(IIIa)}$$

can be obtained, wherein, in the general formula (IIIa), $R^2$ represents an acyl group selected from —C(O)—CH$_3$ (acetyl group) or —C(O)—C$_2$H$_5$ (propionyl group), preferably —C(O)—CH$_3$ (acetyl group), $R^3$ represents a linear or branched, saturated or mono- or polyunsaturated aliphatic $C_{10}$-$C_{30}$-alkyl radical, preferably $C_{10}$-$C_{24}$-alkyl radical.

Especially, the radical $R^3$ in the general formula (IIIa) can represent a 1-decanyl radical, a 1-dodecanyl radical (lauryl radical), a 1-tetradecanyl radical (myristyl radical), a 1-hexadecanyl radical (cetyl radical), a 1-heptadecanyl radical (margaryl radical), a 1-octadecanyl radical (stearyl radical), a 1-eicosanyl radical (arachidyl radical), a 1-docosanyl radical (behenyl radical), a 1-tetracosanyl radical (ligoceryl radical), a 1-hexacosanyl radical (ceryl radical), a 1-octacosanyl radical (montanyl radical), a 1-tricontanyl radical (melissyl radical), a cis-9-hexadecen-1-yl radical (palmitoleyl radical), a cis-9-octadecen-1-yl radical (oleyl radical), a trans-9-octadecen-1-yl radical (elaidyl radical), a cis-11-octadecen-1-yl radical, a cis,cis-9,12-octadecadien-1-yl radical (linoleyl radical) or a 6,9,12-octadecatrien-1-yl radical (γ-linolenyl radical), preferably a cis-9-octadecen-1-yl radical (oleyl radical).

Further Description of the Inventive Method in General, Especially According to Both Synthesis Route (A) and Synthesis Route (B)

All the following explanations refer to the inventive method as a whole or as such, i.e. to both synthesis route (A) and synthesis route (B) of the inventive method.

According to both synthesis route (A) and synthesis route (B) of the inventive method, a fatty alcohol (II) selected from $C_{10}$-$C_{30}$-fatty alcohols, especially $C_{10}$-$C_{24}$-fatty alcohols, is used as reactant.

According to a particular embodiment of the inventive method, it may especially be provided that the fatty alcohol (II) used in the inventive method corresponds to the general formula (II')

$$R^3-OH \quad \text{(II')}$$

wherein the radical $R^3$ represents a linear or branched, saturated or mono- or polyunsaturated aliphatic $C_{10}$-$C_{30}$-alkyl radical, preferentially $C_{10}$-$C_{24}$-alkyl radical, especially wherein the hydroxyl function (OH-function) is primary and/or terminal.

Especially, it is preferred in this context according to the invention if, in the general formula (II'), the radical $R^3$ represents a linear, saturated or mono- or polyunsaturated aliphatic $C_{10}$-$C_{24}$-alkyl radical; especially the hydroxyl function (OH function) is primary and/or terminal.

Especially, it is further preferred in this context according to the invention if, in the general formula (II'), the radical $R^3$ represents a 1-decanyl radical, a 1-dodecanyl radical (lauryl radical), a 1-tetradecanyl radical (myristyl radical), a 1-hexadecanyl radical (cetyl radical), a 1-heptadecanyl radical (margaryl radical), a 1-octadecanyl radical (stearyl radical), a 1-eicosanyl radical (arachidyl radical), a 1-docosanyl radical (behenyl radical), a 1-tetracosanyl radical (ligoceryl radical), a 1-hexacosanyl radical (ceryl radical), a 1-octacosanyl radical (montanyl radical), a 1-tricontanyl radical (melissyl radical), a cis-9-hexadecen-1-yl radical (palmitoleyl radical), a cis-9-octadecen-1-yl radical (oleyl radical), a trans-9-octadecen-1-yl radical (elaidyl radical), a cis-11-octadecen-1-yl radical, a cis,cis-9,12-octadecadien-1-yl radical (linoleyl radical) or a 6,9,12-octadecatrien-1-yl radical (γ-linolenyl radical), preferably a cis-9-octadecen-1-yl radical (oleyl radical).

Especially, the fatty alcohol (II), which can be used in the inventive method, can be selected from linear or branched, saturated or mono- or polyunsaturated aliphatic $C_{10}$-$C_{30}$-fatty alcohols, especially $C_{10}$-≤$C_{24}$-fatty alcohols, preferentially with a primary and/or terminal hydroxyl function (OH-function).

According to a particular embodiment of the inventive method, the fatty alcohol (II) may be selected from linear, saturated or mono- or polyunsaturated, aliphatic monohydric and preferably primary $C_{10}$-$C_{30}$-fatty alcohols, especially linear, saturated or mono- or polyunsaturated, aliphatic monohydric and preferably primary $C_{10}$-$C_{24}$-fatty alcohols.

According to a further particular embodiment of inventive method, the fatty alcohol (II) may be selected from the group of 1-decanol, 1-dodecanol (lauryl alcohol), 1-tetradecanol (myristyl alcohol), 1-hexadecanol (cetyl alcohol), 1-heptadecanol (margaryl alcohol), 1-octadecanol (stearyl alcohol), 1-eicosanol (arachidyl alcohol), 1-docosanol (behenyl alcohol), 1-tetracosanol (ligoceryl alcohol), 1-hexacosanol (ceryl alcohol), 1-octacosanol (montanyl alcohol), 1-tricontanol (melissyl alcohol), cis-9-hexadecen-1-ol (palmitoleyl alcohol), cis-9-octadecen-1-ol (oleyl alcohol), trans-9-octadecen-1-ol (elaidyl alcohol), cis-1-octadecen-1-ol, cis,cis-9,12-octadecadien-1-ol (linoleyl alcohol), 6,9,12-octadecatrien-1-ol (γ-linolenyl alcohol), and combinations thereof, preferably cis-9-octadecen-1-ol (oleyl alcohol).

The aforementioned fatty alcohols (II) are commercially available chemical products or readily available elsewhere.

As far as the reaction products obtainable in the inventive method are concerned—as previously stated—as a reaction product (III) of the inventive method (both according to synthesis route (A) and according to synthesis route (B)), in each case a $C_{10}$-$C_{30}$-fatty alcohol ester of 3-hydroxybutyric acid, especially a $C_{10}$-$C_{24}$-fatty alcohol ester of 3-hydroxybutyric acid, are obtained.

Especially, in the course of the inventive method, as a reaction product (III), a $C_{10}$-$C_{30}$-fatty alcohol ester of 3-hydroxybutyric acid, especially a $C_{10}$-$C_{24}$-fatty alcohol ester of 3-hydroxybutyric acid, preferentially a linear or branched, saturated or mono- or polyunsaturated aliphatic $C_{10}$-$C_{30}$-fatty alcohol ester of 3-hydroxybutyric acid, preferably a linear or branched, saturated or mono- or polyunsaturated aliphatic $C_{10}$-$C_{24}$-fatty alcohol ester of 3-hydroxybutyric acid, can be obtained.

Especially, in the course of the inventive method, as a reaction product (III), a carboxylic acid ester of 3-hydroxybutyric acid derived from a $C_{10}$-$C_{30}$-fatty alcohol, especially a carboxylic acid ester of 3-hydroxybutyric acid derived from a $C_{10}$-$C_{24}$-fatty alcohol, preferentially a carboxylic acid ester of 3-hydroxybutyric acid derived from a linear or branched, saturated or mono- or polyunsaturated $C_{10}$-$C_{30}$-fatty alcohol, preferably a carboxylic acid ester of 3-hydroxybutyric acid derived from a linear or branched, saturated or mono- or polyunsaturated, aliphatic monohydric and preferably primary $C_{10}$-$C_{24}$-fatty alcohol, can be obtained.

Within the scope of the inventive method, the $C_{10}$-$C_{30}$-fatty alcohol, especially $C_{10}$-$C_{24}$-fatty alcohol, may be selected from the group of 1-decanol, 1-dodecanol (lauryl alcohol), 1-tetradecanol (myristyl alcohol), 1-hexadecanol (cetyl alcohol), 1-heptadecanol (margaryl alcohol), 1-octadecanol (stearyl alcohol), 1-eicosanol (arachidyl alcohol), 1-docosanol (behenyl alcohol), 1-tetracosanol (ligoceryl alcohol), 1-hexacosanol (ceryl alcohol), 1-octacosanol (montanyl alcohol), 1-tricontanol (melissyl alcohol), cis-9-hexadecen-1-ol (palmitoleyl alcohol), cis-9-octadecen-1-ol (oleyl alcohol), trans-9-octadecen-1-ol (elaidyl alcohol), cis-11-octadecen-1-ol, cis,cis-9,12-octadecadien-1-ol (linoleyl alcohol), 6,9,12-octadecatrien-1-ol (γ-linolenyl alcohol), and combinations thereof, preferably cis-9-octadecen-1-ol (oleyl alcohol).

According to a particular embodiment of the inventive method, as a reaction product (III), a fatty alcohol ester of 3-hydroxybutyric acid of the general formula (III')

$$CH_3—CH(OH)—CH_2—C(O)OR^3 \quad (III')$$

may be obtained,
wherein the radical $R^3$ represents a linear or branched, saturated or mono- or polyunsaturated aliphatic $C_{10}$-$C_{30}$-alkyl radical, preferentially $C_{10}$-$C_{24}$-alkyl radical.

According to a further particular embodiment of the inventive method, as a reaction product (III), a fatty alcohol ester of 3-hydroxybutyric acid of the aforedefined general formula (III') may be obtained, wherein, in the general formula (III'), the radical $R^3$ represents a linear, saturated or mono- or polyunsaturated $C_{10}$-$C_{24}$-aliphatic alkyl radical.

According to a further particular embodiment of the inventive method, as a reaction product (III), a fatty alcohol ester of 3-hydroxybutyric acid of the aforedefined general formula (III') may be obtained, wherein, in the general formula (III'), the radical $R^3$ represents a 1-decanyl radical, a 1-dodecanyl radical (lauryl radical), a 1-tetradecanyl radical (myristyl radical), a 1-hexadecanyl radical (cetyl radical), a 1-heptadecanyl radical (margaryl radical), a 1-octadecanyl radical (stearyl radical), a 1-eicosanyl radical (arachidyl radical), a 1-docosanyl radical (behenyl radical), a 1-tetracosanyl radical (ligoceryl radical), a 1-hexacosanyl radical (ceryl radical), a 1-octacosanyl radical (montanyl radical), a 1-tricontanyl radical (melissyl radical), a cis-9-hexadecen-1-yl radical (palmitoleyl radical), a cis-9-octadecen-1-yl (oleyl radical), a trans-9-octadecen-1-yl (elaidyl radical), a cis-11-octadecen-1-yl radical, a cis,cis-9,12-octadecadien-1-yl radical (linoleyl radical) or a 6,9,12-octadecatrien-1-yl radical (γ-linolenyl radical), preferably a cis-9-octadecen-1-yl radical (oleyl radical).

As already stated hereinabove, the applicant has completely surprisingly found out that the aforedefined reaction products (i.e. fatty alcohol esters of 3-hydroxybutyric acid) obtainable according to inventive method represent efficient, since physiologically compatible precursors and/or metabolites of 3-hydroxybutyric acid or salts thereof, which can also be used pharmaceutically or clinically in larger quantities, since they are physiologically compatible; these reaction products therefore represent a physiologically and pharmacologically relevant alternative to the free 3-hydroxybutyric acid or salts thereof.

Within the scope of the inventive production method, the reaction product and its formation, especially conversion and yield as well as selectivity, can be controlled and/or regulated by means of the reaction conditions, especially by selecting the reaction temperature (conversion temperature) and/or selecting the reaction pressure (conversion pressure) and/or providing a catalyst and its selection in terms of type and/or amount and/or selecting the amounts of starting compounds (reactants) and/or providing for the removal of by-products.

Following the reaction, the reaction product obtained can be subjected to further conventional or per se known purification or work-up steps.

In this context, the reaction product obtained can be worked up or purified by distillation and/or chromatography after the reaction has taken place.

Also, in accordance with the invention, unreacted starting compounds (Ia) or (Ib) and/or (II) can be separated from the reaction product (III) and/or, in the case of synthesis route (B), from the reaction intermediate (IIIa) and subsequently recycled. This approach leads to improved process economy, especially in the case of large-scale or industrial implementation.

A preferred approach according to the invention both according to synthesis route (A) and according to synthesis route (B) is illustrated by the following reaction or synthesis scheme (wherein compounds (Ia), (Ib), (II), (III/III') and (IIIa) described therein each have the meaning defined hereinabove, including radicals $R^1$, $R^2$ and $R^3$ used therein):

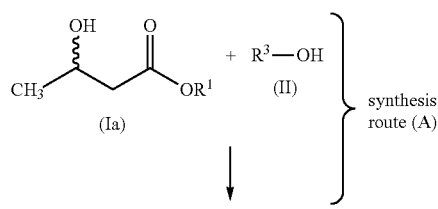

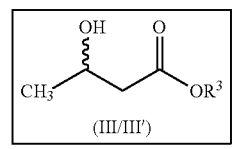

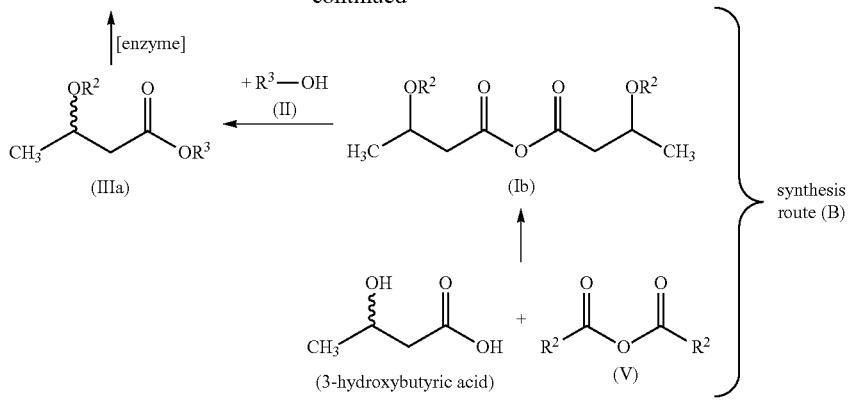

(IIIa)    (Ib)    synthesis route (B)

(3-hydroxybutyric acid)    (V)

A further subject-matter—according to a second aspect of the present invention—is the reaction product obtainable according to the inventive method (as described hereinabove) or the inventive reaction product (i.e. a $C_{10}$-$C_{30}$-fatty alcohol ester of 3-hydroxybutyric acid, especially a $C_{10}$-$C_{24}$-fatty alcohol ester of 3-hydroxybutyric acid). Especially, the reaction product according to the invention is obtainable by synthesis route (A) and/or synthesis route (B).

Especially, the object of the present invention—according to this aspect of the invention—is a fatty alcohol ester of 3-hydroxybutyric acid, especially a reaction product as defined hereinabove (i.e. a fatty alcohol ester obtainable according to the aforedescribed inventive method or an inventive fatty alcohol ester), wherein the fatty alcohol ester of 3-hydroxybutyric acid is a $C_{10}$-$C_{30}$-fatty alcohol ester of 3-hydroxybutyric acid, especially a $C_{10}$-$C_{24}$-fatty alcohol ester of 3-hydroxybutyric acid, preferentially a linear or branched, saturated or mono- or polyunsaturated aliphatic $C_{10}$-$C_{30}$-fatty alcohol ester of 3-hydroxybutyric acid, preferably a linear or branched, saturated or mono- or polyunsaturated aliphatic $C_{10}$-$C_{24}$-fatty alcohol ester of 3-hydroxybutyric acid According to a particular embodiment according to this aspect of the invention, the object of the present invention is a fatty alcohol ester of 3-hydroxybutyric acid, especially as defined hereinabove, especially a reaction product as defined hereinabove, wherein the fatty alcohol ester of 3-hydroxybutyric acid is a carboxylic acid ester of 3-hydroxybutyric acid derived from a $C_{10}$-$C_{30}$-fatty alcohol, especially a carboxylic acid ester of 3-hydroxybutyric acid derived from a $C_{10}$-$C_{24}$-fatty alcohol, preferentially a carboxylic acid ester of 3-hydroxybutyric acid derived from a linear or branched, saturated or mono- or polyunsaturated, $C_{10}$-$C_{30}$-fatty alcohol, preferably a carboxylic acid ester of 3-hydroxybutyric acid derived from a linear or branched, saturated or mono- or polyunsaturated, aliphatic monohydric and preferably primary $C_{10}$-$C_{24}$-fatty alcohol.

In this context, the $C_{10}$-$C_{30}$-fatty alcohol, especially $C_{10}$-$C_{24}$-fatty alcohol, from which the aforedefined inventive fatty alcohol ester of 3-hydroxybutyric acid is derived, is especially selected from the group of 1-decanol, 1-dodecanol (lauryl alcohol), 1-tetradecanol (myristyl alcohol), 1-hexadecanol (cetyl alcohol), 1-heptadecanol (margaryl alcohol), 1-octadecanol (stearyl alcohol), 1-eicosanol (arachidyl alcohol), 1-docosanol (behenyl alcohol), 1-tetracosanol (ligoceryl alcohol), 1-hexacosanol (ceryl alcohol), 1-octacosanol (montanyl alcohol), 1-tricontanol (melissyl alcohol), cis-9-hexadecen-1-ol (palmitoleyl alcohol), cis-9-octadecen-1-ol (oleyl alcohol), trans-9-octadecen-1-ol (elaidyl alcohol), cis-1-octadecen-1-ol, cis,cis-9,12-octadecadien-1-ol (linoleyl alcohol), 6,9,12-octadecatrien-1-ol (γ-linolenyl alcohol), and combinations thereof, preferably cis-9-octadecen-1-ol (oleyl alcohol)

According to another particular embodiment according to this aspect of the invention, the object of the present invention is a fatty alcohol ester of 3-hydroxybutyric acid, especially as defined hereinabove, especially a reaction product as defined hereinabove, wherein the fatty alcohol ester of 3-hydroxybutyric acid corresponds to the general formula (III')

$$CH_3—CH(OH)—CH_2—C(O)OR^3 \qquad (III')$$

wherein the radical $R^3$ represents a linear or branched, saturated or mono- or polyunsaturated aliphatic $C_{10}$-$C_{30}$-alkyl radical, preferentially a $C_{10}$-$C_{24}$-alkyl radical.

According to the invention, it is particularly preferred in this context if, in the general formula (III'), the radical $R^3$ represents a linear, saturated or mono- or polyunsaturated aliphatic $C_{10}$-$C_{24}$-alkyl radical.

In accordance with the invention, it is equally particularly preferred in this context if, in the general formula (III'), the radical $R^3$ represents a 1-decanyl radical, a 1-dodecanyl radical (lauryl radical), a 1-tetradecanyl radical (myristyl radical), a 1-hexadecanyl radical (cetyl radical), a 1-heptadecanyl radical (margaryl radical), a 1-octadecanyl radical (stearyl radical), a 1-eicosanyl radical (arachidyl radical), a 1-docosanyl radical (behenyl radical), a 1-tetracosanyl radical (ligoceryl radical), a 1-hexacosanyl radical (ceryl radical), a 1-octacosanyl radical (montanyl radical), a 1-tricontanyl radical (melissyl radical), a cis-9-hexadecen-1-yl radical (palmitoleyl radical), a cis-9-octadecen-1-yl radical (oleyl radical), a trans-9-octadecen-1-yl radical (elaidyl radical), a cis-11-octadecen-1-yl radical, a cis,cis-9,12-octadecadien-1-yl radical (linoleyl radical) or a 6,9,12-octadecatrien-1-yl radical (γ-linolenyl radical), preferably a cis-9-octadecen-1-yl radical (oleyl radical).

As already mentioned, the applicant has completely surprisingly found out that also the reaction intermediates formed according to synthesis route (B) before hydrolysis of the acyl group (i.e. fatty alcohol esters of the acylated 3-hydroxybutyric acid or synonymously also fatty alcohol esters of the 3-acyloxybutyric acid) represent efficient, since physiologically compatible precursors and/or metabolites of the 3-hydroxybutyric acid or its salts, which can be used pharmaceutically or clinically also in larger quantities, as they are physiologically compatible; these reaction intermediates therefore equally represent a physiologically and pharmacologically relevant alternative to the free 3-hydroxybutyric acid or its salts.

The object of the present invention—according to the second aspect of the invention—is therefore also, according to a particular embodiment, a reaction intermediate, especially a (chemical) product, especially a reaction intermediate (IIIa), preferably a fatty alcohol ester of acylated 3-hydroxybutyric acid (3-acyloxybutyric acid), which is obtainable according to the method defined hereinabove according to synthesis route (B) before hydrolysis of the acyl group.

The object of the present invention—according to this particular embodiment—is especially a fatty alcohol ester of acylated 3-hydroxybutyric acid (3-acyloxybutyric acid), especially a reaction intermediate as defined hereinabove, wherein the fatty alcohol ester of acylated 3-hydroxybutyric acid (3-acyloxybutyric acid) is a $C_{10}$-$C_{30}$-fatty alcohol ester of acylated 3-hydroxybutyric acid (3-acyloxybutyric acid), especially a $C_{10}$-$C_{24}$-fatty alcohol ester of acylated 3-hydroxybutyric acid (3-acyloxybutyric acid), preferentially a linear or branched, $C_{10}$-$C_{30}$-saturated or mono- or polyunsaturated aliphatic fatty alcohol ester of acylated 3-hydroxybutyric acid (3-acyloxybutyric acid), preferably a linear or branched, saturated or mono- or polyunsaturated $C_{10}$-$C_{24}$-aliphatic fatty alcohol ester of acylated 3-hydroxybutyric acid (3-acyloxybutyric acid).

Especially, the object of the present invention—according to this particular embodiment—is a fatty alcohol ester of acylated 3-hydroxybutyric acid (3-acyloxybutyric acid), especially as defined hereinabove, especially a reaction intermediate as defined hereinabove, wherein the fatty alcohol ester of the acylated 3-hydroxybutyric acid (3-acyloxybutyric acid) is a carboxylic acid ester of the acylated 3-hydroxybutyric acid (3-acyloxybutyric acid) derived from a $C_{10}$-$C_{30}$-fatty alcohol, especially a carboxylic acid ester of acylated 3-hydroxybutyric acid (3-acyloxybutyric acid) derived from a $C_{10}$-$C_{24}$-fatty alcohol, preferentially a carboxylic acid ester of the acylated 3-hydroxybutyric acid (3-acyloxybutyric acid) derived from a linear or branched, saturated or mono- or polyunsaturated, aliphatic monovalent and preferably primary $C_{10}$-$C_{30}$-fatty alcohol, preferably a carboxylic acid ester of the acylated 3-hydroxybutyric acid (3-acyloxybutyric acid) derived from a linear or branched, saturated or mono- or polyunsaturated, aliphatic monovalent and preferably primary $C_{10}$-$C_{24}$-fatty alcohol.

In this context, it is particularly preferred according to the invention if the $C_{10}$-$C_{30}$-fatty alcohol, especially $C_{10}$-$C_{24}$-fatty alcohol, from which the inventive aforedefined fatty alcohol ester of acylated 3-hydroxybutyric acid is derived, is selected from the group of 1-decanol, 1-dodecanol (lauryl alcohol), 1-tetradecanol (myristyl alcohol), 1-hexadecanol (cetyl alcohol), 1-heptadecanol (margaryl alcohol), 1-octadecanol (stearyl alcohol), 1-eicosanol (arachidyl alcohol), 1-docosanol (behenyl alcohol), 1-tetracosanol (ligoceryl alcohol), 1-hexacosanol (ceryl alcohol), 1-octacosanol (montanyl alcohol), 1-tricontanol (melissyl alcohol), cis-9-hexadecen-1-ol (palmitoleyl alcohol), cis-9-octadecen-1-ol (oleyl alcohol), trans-9-octadecen-1-ol (elaidyl alcohol), cis-11-octadecen-1-ol, cis,cis-9,12-octadecadien-1-ol (linoleyl alcohol), 6,9,12-octadecatrien-1-ol (γ-linolenyl alcohol), and combinations thereof, preferably cis-9-octadecen-1-ol (oleyl alcohol).

According to the invention, in this context it is preferred if the acylated 3-hydroxybutyric acid (3-acyloxybutyric acid) is an acetylated 3-hydroxybutyric acid (3-acetoxybutyric acid).

Especially, the object of the present invention—according to this particular embodiment—is also a fatty alcohol ester of acylated 3-hydroxybutyric acid (3-acyloxybutyric acid), especially as defined hereinabove, especially a reaction intermediate as defined hereinabove, wherein the fatty alcohol ester of acylated 3-hydroxybutyric acid (3-acyloxybutyric acid) is a carboxylic acid ester of acylated 3-hydroxybutyric acid (3-acyloxybutyric acid) derived from a linear, saturated or mono- or polyunsaturated aliphatic, monohydric primary $C_{10}$-$C_{24}$-fatty alcohol.

Finally, the object of the present invention—according to this particular embodiment—is equally a fatty alcohol ester of acylated 3-hydroxybutyric acid (3-acyloxybutyric acid), especially as defined hereinabove, especially a reaction intermediate as defined hereinabove, wherein the fatty alcohol ester of acylated 3-hydroxybutyric acid (3-acyloxybutyric acid) is a fatty alcohol ester of acylated 3-hydroxybutyric acid (3-acyloxybutyric acid) of the general formula (IIIa)

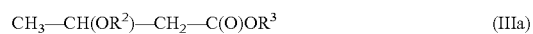

$$CH_3-CH(OR^2)-CH_2-C(O)OR^3 \quad\quad (IIIa)$$

wherein, in the general formula (IIIa),
$R^2$ represents an acyl group selected from —C(O)—$CH_3$ (acetyl group) or —C(O)—$C_2H_5$ (propionyl group), preferably —C(O)—$CH_3$ (acetyl group),
$R^3$ represents a linear or branched, saturated or mono- or polyunsaturated aliphatic $C_{10}$-$C_{30}$-alkyl radical, preferentially $C_{10}$-$C_{24}$-alkyl radical.

Especially, the radical $R^3$ can represent a 1-decanyl radical, a 1-dodecanyl radical (lauryl radical), a 1-tetradecanyl radical (myristyl radical), a 1-hexadecanyl radical (cetyl radical), a 1-heptadecanyl radical (margaryl radical), a 1-octadecanyl radical (stearyl radical), a 1-eicosanyl radical (arachidyl radical), a 1-docosanyl radical (behenyl radical), a 1-tetracosanyl radical (ligoceryl radical), a 1-hexacosanyl radical (ceryl radical), a 1-octacosanyl radical (montanyl radical), a 1-tricontanyl radical (melissyl radical), a cis-9-hexadecen-1-yl radical (palmitoleyl radical), a cis-9-octadecen-1-yl radical (oleyl radical), a trans-9-octadecen-1-yl radical (elaidyl radical), a cis-11-octadecen-1-yl radical, a cis,cis-9,12-octadecadien-1-yl radical (linoleyl radical) or a 6,9,12-octadecatrien-1-yl radical (γ-linolenyl radical), preferably a cis-9-octadecen-1-yl radical (oleyl radical).

The reaction product obtainable according to the inventive method or the inventive reaction product, as defined hereinabove, respectively, and/or the fatty alcohol ester of 3-hydroxybutyric acid, as defined hereinabove, or the fatty alcohol ester of acylated 3-hydroxybutyric acid (3-acyloxybutyric acid) (=intermediate reaction product before hydrolysis according to synthesis route (B)), as defined hereinabove, obtainable according to the inventive production method or the inventive fatty alcohol ester of 3-hydroxybutyric acid, as defined hereinabove, as well as the fatty alcohol ester of acylated 3-hydroxybutyric acid (3-acyloxybutyric acid), as defined hereinabove, respectively, comprises a multitude of advantages and special features compared to the prior art:

As the applicant has surprisingly found out, the reaction product obtainable according to the inventive method or the inventive reaction product, as defined hereinabove, respectively, and/or or the fatty alcohol ester of 3-hydroxybutyric acid, as defined hereinabove, or the fatty alcohol ester of acylated 3-hydroxybutyric acid (3-acyloxybutyric acid), as defined hereinabove, obtainable according to the inventive production method or the or the inventive fatty alcohol ester of 3-hydroxybutyric acid, as defined hereinabove, as well as the inventive fatty alcohol ester of acylated 3-hydroxybutyric acid (3-acyloxybutyric acid), as defined hereinabove, respectively, are suitable as a precursor or metabolite of 3-hydroxybutyric acid or its salts, since, on the one hand, these compounds are converted physiologically, especially in the gastrointestinal tract, to 3-hydroxybutyric acid or its salts and, on the other hand, they simultaneously comprise a good physiological compatibility or tolerability, especially with regard to non-toxicity and acceptable organoleptic properties.

Moreover, the reaction product obtainable according to the inventive method or the inventive reaction product as defined hereinabove, respectively, and/or the fatty alcohol ester of 3-hydroxybutyric acid, as defined hereinabove, as well as the fatty alcohol ester of acylated 3-hydroxybutyric acid (3-acyloxybutyric acid), as defined hereinabove, obtainable according to the inventive production method or the inventive fatty alcohol ester of 3-hydroxybutyric acid, as defined hereinabove, as well as the inventive fatty alcohol ester of acylated 3-hydroxybutyric acid (3-acyloxybutyric acid), as defined hereinabove, respectively, are easily accessible or available on a large scale on a synthetic basis, even on a commercial scale, and with the required pharmaceutical or pharmacological quality.

Additionally, the reaction product obtainable according to the inventive method or the inventive reaction product, as defined hereinabove, respectively, and/or the fatty alcohol ester of 3-hydroxybutyric acid, as defined hereinabove, as well as the fatty alcohol ester of acylated 3-hydroxybutyric acid (3-acyloxybutyric acid), as defined hereinabove, obtainable according to the inventive production method or the inventive fatty alcohol ester of 3-hydroxybutyric acid, as defined hereinabove, as well as the inventive fatty alcohol ester of acylated 3-hydroxybutyric acid (3-acyloxybutyric acid), as defined hereinabove, respectively, can, if necessary, be provided in enantiomerically pure or enantiomerically enriched form.

The reaction product obtainable according to the inventive method or the inventive reaction product, as defined hereinabove, respectively, and/or the fatty alcohol ester of 3-hydroxybutyric acid, as defined hereinabove, as well as the fatty alcohol ester of acylated 3-hydroxybutyric acid (3-acyloxybutyric acid), as defined hereinabove, obtainable according to the inventive production method or the inventive fatty alcohol ester of 3-hydroxybutyric acid, as defined hereinabove, as well as the inventive fatty alcohol ester of acylated 3-hydroxybutyric acid (3-acyloxybutyric acid), as defined hereinabove, respectively, thus represent an efficient pharmacological drug target in the context of keto-body therapy of the human or animal body.

In the following, the remaining aspects of the invention are explained in more detail.

A further subject-matter of the present invention—according to a third aspect of the present invention—is a pharmaceutical composition, especially a drug (pharmaceutical) or medicament, which comprises a reaction product obtainable according to the inventive production method or the inventive reaction product, as defined hereinabove, respectively, or a fatty alcohol ester of 3-hydroxybutyric acid, as defined hereinabove, and/or a fatty alcohol ester of acylated 3-hydroxybutyric acid (3-acyloxybutyric acid), as defined hereinabove, obtainable according to the inventive production method or the inventive fatty alcohol ester of 3-hydroxybutyric acid, as defined hereinabove, and/or the inventive fatty alcohol ester of acylated 3-hydroxybutyric acid (3-acyloxybutyric acid) (=intermediate reaction product before hydrolysis according to synthesis route (B)), as defined hereinabove, respectively.

Especially, according to this aspect of the invention, the present invention relates to a pharmaceutical composition for the prophylactic and/or therapeutic treatment or for use in the prophylactic and/or therapeutic treatment of diseases of the human or animal body. This may especially concern diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Again, a further subject-matter of the present invention—according to a fourth aspect of the present invention—is a reaction product obtainable according to the inventive production method or the inventive reaction product, as defined hereinabove, respectively, or a fatty alcohol ester of 3-hydroxybutyric acid, as defined hereinabove, and/or a fatty alcohol ester of acylated 3-hydroxybutyric acid (3-acyloxybutyric acid), as defined hereinabove, obtainable according to the inventive production method or the inventive fatty alcohol ester of 3-hydroxybutyric acid, as defined hereinabove, and/or the inventive fatty alcohol ester of acylated 3-hydroxybutyric acid (3-acyloxybutyric acid), as defined hereinabove, respectively, for the prophylactic and/or therapeutic treatment or for use in the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a fifth aspect of the present invention—is the use of a reaction product, as defined hereinabove, obtainable according to the inventive production method or the inventive reaction product, as defined hereinabove, respectively, or a fatty alcohol ester of 3-hydroxybutyric acid, as defined hereinabove, and/or a fatty alcohol ester of acylated 3-hydroxybutyric acid (3-acyloxybutyric acid), as defined hereinabove, obtainable according to the inventive production method or the inventive fatty alcohol ester of 3-hydroxybutyric acid, as defined hereinabove, and/or the inventive fatty alcohol ester of acylated 3-hydroxybutyric acid (3-acyloxybutyric acid), as defined hereinabove, respectively, for the prophylactic and/or therapeutic treatment or for producing a pharmaceutical for the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a sixth aspect of the present invention—is the use of a reaction product obtainable according to the inventive production method or the inventive reaction product, as defined hereinabove, respectively, or a fatty alcohol ester of 3-hydroxybutyric acid, as defined hereinabove, and/or a fatty alcohol ester of acylated 3-hydroxybutyric acid (3-acyloxybutyric acid), as defined hereinabove, obtainable according to the inventive production method or the inventive fatty alcohol ester of 3-hydroxybutyric acid, as defined hereinabove, and/or the inventive fatty alcohol ester of acylated 3-hydroxybutyric acid (3-acyloxybutyric acid), as defined hereinabove, respectively, for the prophylactic and/or therapeutic treatment or for producing a medicament for the prophylactic and/or therapeutic treatment of or for the application for catabolic metabolic states, such as hunger, diets or low-carbohydrate nutrition.

Likewise, a further subject-matter of the present invention—according to a seventh aspect of the present invention—is a food and/or a food product, which comprises a reaction product obtainable according to the inventive production method or the inventive reaction product, as defined hereinabove, respectively, or a fatty alcohol ester of 3-hydroxybutyric acid, as defined hereinabove, and/or a fatty alcohol ester of acylated 3-hydroxybutyric acid (3-acyloxybutyric acid), as defined hereinabove, obtainable according to the inventive production method or the inventive fatty alcohol ester of 3-hydroxybutyric acid, as defined hereinabove, and/or the inventive fatty alcohol ester of acylated 3-hydroxybutyric acid (3-acyloxybutyric acid), as defined hereinabove, respectively.

According to a particular embodiment, the food and/or the food product may essentially be a dietary supplement, a functional food, a novel food, a food additive, a food supplement, a dietary food, a power snack, an appetite suppressant or a strength and/or endurance sport supplement.

Finally, yet another subject-matter of the present invention—according to an eighth aspect of the present invention—is the use of a reaction product, as defined hereinabove, obtainable according to the inventive production method or in the inventive reaction product, as defined hereinabove, respectively or a fatty alcohol ester of 3-hydroxybutyric acid, as defined hereinabove, and/or a fatty alcohol ester of acylated 3-hydroxybutyric acid (3-acyloxybutyric acid), as defined hereinabove, obtainable according to the inventive production method or the inventive fatty alcohol ester of 3-hydroxybutyric acid, as defined hereinabove, and/or the inventive fatty alcohol ester of acylated 3-hydroxybutyric acid (3-acyloxybutyric acid), as defined hereinabove, respectively, in a food and/or a food product.

According to this aspect of the invention, the food and/or the food product may especially be a dietary supplement, a functional food, a novel food, a food additive, a food supplement, a dietary food, a power snack, an appetite suppressant or a strength and/or endurance sports supplement.

Further embodiments, modifications and variations of the present invention are readily recognizable or realizable by a person skilled in the art when reading the description, without leaving the scope of the present invention.

The present invention is illustrated by the following examples, which are not intended to limit the present invention in any way, but only to explain the exemplary and non-limiting implementation and configuration of the present invention.

EXAMPLES

Abbreviations Used

3-BHB ethyl=3-hydroxybutyric acid ethyl ester
3-BHB-decyl=3-hydroxybutyric acid decyl ester
3-BHB oleyl=3-hydroxybutyric acid oleyl ester
dimer(s)=dimer(s) of 3-hydroxybutyric acid and/or ethyl 3-hydroxybutyric acid ester (reaction by-products).

Examples of Production

The inventive production method is illustrated by the following examples. The general reaction scheme for this is shown and explained in the general description section.

Production of 3-BHB-Decyl Ester According to Synthesis Route (A)

In a 500-ml-multi-neck flask with dephlegmator (partial condenser) and distillation bridge, 132 g (R)/(S)-3-hydroxybutyric acid ethyl ester, 158 g 1-decanol and 2.9 g immobilized enzyme (CALB lipase on polymer support, derived from *Candida antarctica*, e.g. Novozym® 435 from Sigma-Aldrich or Merck or Lipozym® 435 from Strem Chemicals, Inc.) are provided.

The reaction mixture is reacted under stirring at 70° C. and under vacuum (<500 mbar) for 7 h. The enzyme is then filtered out and the excess 3-hydroxybutyric acid ethyl ester or the excess 1-decanol is distilled off under vacuum. The residue obtained is steam-treated in a high vacuum for 2 to 4 h (steam temperature 160° C.). Pure 3-BHB-decyl ester is obtained.

Production of 3-BHB-Oleyl Ester According to Synthesis Route (A)

In a 500-ml-multi-neck flask with dephlegmator (partial condenser) and distillation bridge, 132 g (R)/(S)-3-hydroxybutyric acid ethyl ester, 270 g oleyl alcohol (purity: 85%) and 4.0 g immobilized enzyme (CALB lipase on polymer support, derived from *Candida antarctica*, e.g. Novozym® 435 from Sigma-Aldrich or Merck or Lipozym® 435 from Strem Chemicals Inc.) are provided.

The reaction mixture is reacted under stirring at 70° C. and under vacuum (<500 mbar) for 7 h. To monitor the reaction, samples are taken after 0.5 h, 1 h, 2 h, 3 h, 4 h, 5 h, and 7 h, respectively, and analyzed by GC. The enzyme is then filtered out and the product 3-BHB-oleyl ester is obtained in vacuo by multiple distillation. If necessary, the residue obtained is steam-treated in a high vacuum for 2 to 4 h (steam temperature 160° C.). Pure 3-BHB-oleyl ester is obtained.

TABLE conversion/time curve in the preparation of 3-BHB-oleyl ester (50° C., 50-60 mbar, 24 h, 1% by weight enzyme).

| | peak at [min] | response time [h] | | | | | | |
|---|---|---|---|---|---|---|---|---|
| | | 0 [%] | 0.5 [%] | 1 [%] | 2 [%] | 3 [%] | 4 [%] | 5 [%] | 7 [%] |
| 3-BHB ethyl | 10 | 29.4 | 21.6 | 18.7 | 15.1 | 12.7 | 11.5 | 10.1 | 7.7 |
| dimers | 20 | 0.0 | 0.4 | 0.5 | 0.6 | 0.6 | 0.6 | 0.7 | 0.8 |
| oleyl alcohol | 27 | 70.6 | 56.8 | 48.9 | 40.5 | 34.2 | 29.7 | 28.5 | 24.8 |
| 3-BHB oleyl | 31 | 0.0 | 21.2 | 31.9 | 43.8 | 52.5 | 58.2 | 60.7 | 66.7 |

Production of Further 3-BHB Fatty Alcohol Esters According to Synthesis Route (A)

The above enzyme-catalyzed syntheses are also carried out with other fatty alcohols (namely cetyl alcohol, margaryl alcohol, stearyl alcohol, behenyl alcohol, melissyl alcohol, palmitoleyl alcohol and linoleyl alcohol). The corresponding 3-BHB fatty alcohol esters are obtained in each case as pure substances.

Further Production of 3-BHB Fatty Alcohol Esters According to Synthesis Route (A)

The previous experiments are repeated, however with sodium methylate (NaOMe) as catalyst (1% by weight) instead of the enzyme, 40 mol-% excess 3-BHB ethyl ester and at temperatures between 100 and 120° C. Comparable results are obtained. Purification and separation are carried out in the same way.

Production of 3-BHB Decyl Ester According to Synthesis Route (B)

1. Step: Synthesis of the Acetylated 3-BHB Anhydride

In a 1,000-ml-multi-neck flask with dephlegmator (partial condenser) and distillation bridge 25 g (R)/(S)-3-hydroxybutyric acid are provided in 95 g acetic acid. 90 g acetic anhydride are added to the reaction mixture at 80° C. under N2-atmosphere within one hour. The reaction mixture is stirred at 80° C. for further 4 to 5 hours. 3-Acetoxybutyric anhydride (=acetylated 3-hydroxybutyric anhydride) is formed.

2. Step: Reaction of the Acetylated 3-BHB Anhydride with Fatty Alcohol

Then 30 g 1-decanol are added to the reaction mixture at 80° C. and stirred for 8 to 10 hours. The reaction product of the second stage is a fatty alcohol ester of 3-acetoxybutyric acid (i.e. in other words, a fatty alcohol ester of acetylated 3-hydroxybutyric acid) and an intermediate for the production of the corresponding 3-BHB fatty alcohol ester, but is itself also pharmaceutically applicable or effective for the same intended use.

The by-products formed (acetic acid from the first step and 3-acetoxybutyric acid from the second step) are distilled off under vacuum (<50 mbar) at 100 to 120° C.; pure fatty alcohol ester of 3-acetoxybutyric acid is obtained. Characterization is carried out by GC, GPC and GC-MS.

3. Step: Enzyme-Catalyzed Hydrolysis of the Acetyl Group

Part of this intermediate product from the second step (i.e. fatty alcohol ester of 3-acetoxybutyric acid) is then subjected to hydrolysis of the acetyl group (partial or selective hydrolysis in the presence of enzyme). For this purpose, the reaction product from the second step is reacted in aqueous medium in the presence of immobilized enzyme (CALB lipase on polymer support, derived from *Candida antarctica*, first preparation: Novozym® 435 from Sigma-Aldrich or Merck and second preparation: Lipozym® 435 from Strem Chemicals, Inc.) for 8 hours at 50° C. After separation of the enzyme and subsequent purification by distillation, the fatty alcohol ester of 3-hydroxybutyric acid is obtained as the hydrolysis product, i.e. 3-hydroxybutyric acid decyl ester. Characterization is carried out by GC, GPC and GC-MS.

The remaining portion of the intermediate is used for subsequent efficacy trials.

Further Production of 3-BHB Decyl Ester According to Synthesis Route (B)

The previous experiment is repeated, however, after the reaction of (R)/(S)-3-hydroxybutyric anhydride, the by-product formed in the first step (acetic acid) is first removed by distillation under vacuum (<50 mbar) at 100 to 120° C. and pure 3-acetoxybutyric anhydride is obtained. Characterization is carried out by GC, GPC and GC-MS.

Subsequently, the pure 3-acetoxybutyric anhydride is reacted with 1-decanol, purified and analyzed (as described in the previous experiment) to yield a pure fatty alcohol ester of 3-acetoxybutyric acid.

The reaction product (i.e. fatty alcohol ester of 3-acetoxybutyric acid) is then hydrolyzed as described in the previous experiment to give a fatty alcohol ester of 3-hydroxybutyric acid, i.e. 3-hydroxybutyric acid decyl ester. Characterization is performed by GC, GPC and GC-MS.

Production of 3-BHB Oleyl Ester According to Synthesis Route (B)

1. Step: Synthesis of the Acetylated 3-BHB Anhydride

In a 1,000-ml-multi-neck flask with dephlegmator (partial condenser) and distillation bridge 25 g (R)/(S)-3-hydroxybutyric acid are provided in 95 g acetic acid. Then 90 g acetic anhydride are added to the reaction mixture at 80° C. under N2-atmosphere within one hour. The reaction mixture is stirred at 80° C. for further 4 to 5 hours. 3-Acetoxybutyric anhydride (=acetylated 3-hydroxybutyric anhydride) is formed.

2. Step: Reaction of the Acetylated 3-BHB Anhydride with Fatty Alcohol

Then 52 g oleyl alcohol are added to the reaction mixture at 80° C. and stirred for 8 to 10 hours. The reaction product of the second step is a fatty alcohol ester of 3-acetoxybutyric acid (i.e. in other words, an oleyl alcohol ester of acetylated 3-hydroxybutyric acid) and an intermediate for the preparation of the corresponding 3-BHB fatty alcohol ester, but is itself also pharmaceutically applicable or effective for the same use.

The by-products formed (acetic acid from the first step and 3-acetoxybutyric acid from the second step) are distilled off under vacuum (<50 mbar) at 100 to 120° C.; pure fatty alcohol ester of 3-acetoxybutyric acid is obtained. Characterization is carried out by GC, GPC and GC-MS.

3. Step: Enzyme-Catalyzed Hydrolysis of the Acetyl Group

Part of this intermediate from the second step (i.e. oleyl alcohol ester of 3-acetoxybutyric acid) is then subjected to hydrolysis of the acetyl group (partial or selective hydrolysis in the presence of enzyme). For this purpose, the reaction product from the second step is reacted in aqueous medium in the presence of immobilized enzyme (CALB lipase on polymer support, derived from *Candida antarctica*, first preparation: Novozym® 435 from Sigma-Aldrich or Merck and second preparation: Lipozym® 435 from Strem Chemicals, Inc.) are reacted for 8 hours at 50° C. After separation of the enzyme and subsequent purification by distillation, the fatty alcohol ester of 3-hydroxybutyric acid is obtained as the hydrolysis product, i.e. 3-hydroxybutyric acid oleyl ester. Characterization is carried out by GC, GPC and GC-MS.

The remaining portion of the intermediate is used for subsequent efficacy trials.

Further Production of 3-BHB Oleyl Ester According to Synthesis Route (B)

The previous experiment is repeated, however, after the reaction of (R)/(S)-3-hydroxybutyric anhydride, the by-product formed in the first step (acetic acid) is first removed by distillation under vacuum (<50 mbar) at 100 to 120° C., and pure 3-acetoxybutyric anhydride is obtained. Characterization is carried out by GC, GPC and GC-MS.

Subsequently, the pure 3-acetoxybutyric anhydride is reacted with oleyl alcohol, purified and analyzed (as described in the previous experiment) to yield a pure fatty alcohol ester of 3-acetoxybutyric acid.

The reaction product (i.e. oleyl alcohol ester of 3-acetoxybutyric acid) is then hydrolyzed as described in the previous experiment to give an oleyl alcohol ester of 3-hydroxybutyric acid i.e. 3-hydroxybutyric acid oleyl ester. Characterization is performed by GC, GPC and GC-MS.

Further Production of 3-BHB Fatty Acid Esters According to Synthesis Route (B)

The four preceding experiments are each repeated, however, in the presence of an acidic catalyst.

In a first series of preparations, the reactions of 1-decanol and oleyl alcohol, respectively, are repeated in the presence of sulfuric acid ($H_2SO_4$) as a catalyst and at temperatures between 75 and 110° C. Comparable results are obtained. Purification, separation or fractionation and hydrolysis are carried out in the same way.

In a second series of preparations, the reactions of 1-decanol and oleyl alcohol, respectively, are repeated in the presence of hydrochloric acid (HCl) as a catalyst and at temperatures between 75 and 110° C. Comparable results are obtained. Purification, separation or fractionation and hydrolysis are carried out in the same way.

In a third series of preparations, the reactions of 1-decanol and oleyl alcohol, respectively, are repeated in the presence of phosphoric acid ($H_3PO_4$) as a catalyst and at temperatures between 75 and 110° C. Comparable results are obtained. Purification, separation or fractionation and hydrolysis are carried out in the same way.

Production of Further 3-BHB Fatty Alcohol Esters According to Synthesis Route (B)

The above syntheses (both autocatalytic and mineral acid-catalyzed) are also carried out accordingly for other fatty alcohols (namely for cetyl alcohol, margaryl alcohol, stearyl alcohol, behenyl alcohol, melissyl alcohol, palmitoleyl alcohol and linoleyl alcohol, respectively). The corresponding 3-BHB fatty alcohol esters are—obtained in each case as pure substances.

Physiological Application Tests: In-Vitro Digestion Tests

Digestion Experiments (Splitting or Cleavage Experiments) of the 3-BHB Fatty Alcohol Esters (i.e. Fatty Alcohol Esters of 3-Hydroxybutyric Acid)

By means of cleavage experiments it is shown that 3-BHB-PG(2) esters or their mixtures, including reaction by-products such as dimers etc., produced according to the invention, can be cleaved in the human gastrointestinal tract.

The test substances used are, on the one hand, purified 3-BHB fatty alcohol esters obtained by the method according to the invention (i.e. obtained both by the method according to synthesis route (A) and by the method according to synthesis route (B)) and, on the other hand, purified fatty alcohol esters of acetylated 3-BHB (3-acetoxybutyric acid) obtained as reaction intermediates by the method according to the invention according to synthesis route (B).

Fatty Alcohol Esters Tested:
- 3-BHB decyl ester
- decyl ester of acetylated 3-BHB (decyl alcohol ester of 3-acetoxybutyric acid)
- 3-BHB oleyl ester
- oleyl ester of acetylated 3-BHB (oleyl alcohol ester of 3-acetoxybutyric acid)
- 3-BHB cetyl ester
- 3-BHB margaryl ester
- 3-BHB stearyl ester
- 3-BHB behenyl ester
- 3-BHB melissyl ester
- 3-BHB palmitoyl ester
- 3-BHB linoleyl ester Two media are investigated for the cleavage experiments under near-body conditions:
- FaSSGF, which simulates the stomach
- FaSSIF, which simulates the intestinal tract Both media are from Biorelevant®, Ltd. in the United Kingdom. In addition, in some experiments, porcine pancrease is added to both media (Panzytrat® 40,000, Allergan).

The results of the cleavage experiments in a FaSSGF or FaSSIF medium with Panzytrat® and without Panzytrat® (both 35° C., 24 h) show that the samples hydrolyze under FaSSGF conditions with Panzytrat® and without Panzytrat®; this is mainly due to the low pH value (pH=1.6) of the medium. Under FaSSIF conditions, a lower conversion using Panzytrat® takes place.

Further Digestion Experiments (Cleavage Experiments) of Inventive

3-BHB Fatty Alcohol Esters (i.e. Fatty Alcohol Esters of 3-Hydroxybutyric Acid)

Cleavage Experiments with Pancreatin

In each case, 2 g of the fatty alcohol esters of 3-hydroxybutyric acid prepared as described hereinabove (i.e. obtained both by the method according to synthesis route (A) and by the method according to synthesis route (B)) or their acetylated derivatives are dissolved in 50 g water and 0.5 g (1% by weight) pancreatin is added. The pancreatin is used in the form of the commercially available product Panzytrat® 40,000 from Allergan. The whole mixture is stirred on a hot plate at 50° C.; the course of the reaction is determined and monitored by continuous recording of the acid number over time. The acid number increases over the observation period (cleavage of the 3-BHB fatty alcohol ester or its acyl derivative to the free acid). The conversion/time course of the aqueous cleavage of the mixture of esters according to the invention by means of pancreatin, including the increase in the acid number over time, demonstrates the desired decomposition of the educt mixture to the free acid. This is confirmed by appropriate analysis. The experiment proves that the fatty alcohol esters of 3-hydroxybutyric acid according to the invention (i.e. obtained both by the method according to synthesis route (A), and by the method according to synthesis route (B)) or their acetylated derivatives are suitable physiological precursors for 3-hydroxybutyric acid for the corresponding keto-body therapies.

The previously described cleavage experiments prove that the fatty alcohol esters of 3-hydroxybutyric acid or their acyl derivatives are efficient precursors or metabolites of free hydroxybutyric acid or its salts, especially with regard to their intended effect, which are present in physiologically compatible or physiologically compatible form.

The invention claimed is:

1. A method for producing fatty alcohol esters of 3-hydroxybutyric acid,
   (A) wherein, according to a first synthesis route (A), at least one compound of the general formula (Ia)

$$CH_3-CH(OH)-CH_2-C(O)OR^1 \quad (Ia)$$

wherein, in the general formula (Ia), the radical $R^1$ represents hydrogen or $C_1$-$C_4$-alkyl,
   is reacted with at least one fatty alcohol (II) selected from $C_{10}$-$C_{30}$-fatty alcohols,
   wherein the reaction is carried out in the absence of any solvents,
   wherein the reaction is carried out in the presence of an enzyme as a catalyst, wherein the catalyst is recycled after the reaction, and
   wherein during the reaction, the compound according to the general formula (IVa)

$$R^1-OH \quad (IVa)$$

is formed simultaneously, wherein, in general formula (IVa), the radical $R^1$ represents hydrogen or $C_1$-$C_4$-alkyl, wherein the compound according to the general formula (IVa) is continuously withdrawn from the reaction;
   or else
   (B) wherein, according to a second synthesis route (B), which is alternative to synthesis route (A), at least one compound of the general formula (Ib)

$$CH_3-CH(OR^2)-CH_2-C(O)-O-C(O)-CH_2-CH(OR^2)-CH_3 \quad (Ib)$$

wherein, in the general formula (Ib), the radical $R^2$ represents an acyl group selected from an acetyl group of formula —C(O)—CH$_3$ or a propionyl group of formula —C(O)—C$_2$H$_5$,
   is reacted with at least one fatty alcohol (II) selected from $C_{10}$-$C_{30}$-fatty alcohols, followed by hydrolysis of the acyl group;
   so that, as a reaction product (III), in each case a $C_{10}$-$C_{30}$-fatty alcohol ester of 3-hydroxybutyric acid is obtained.

2. The method according to claim 1,
   wherein, according to synthesis route (A), the enzyme is selected from synthetases, catalases, esterases, lipases and combinations thereof; and
   wherein, according to synthesis route (A), the enzyme is used in immobilized form on a carrier; and
   wherein, according to synthesis route (A), the enzyme is used in amounts, based on the total amount of starting compounds (Ia) and (II), in the range of from 0.001% by weight to 20% by weight.

3. The method according claim 1,
   wherein, according to synthesis route (A), the compound of the general formula (Ia) and the fatty alcohol (II) are used in a molar ratio of compound of the general formula (Ia)/fatty alcohol (II) in a range of from 1:1 to 10:1.

4. The method according to claim 1,
   wherein, according to synthesis route (B), the reaction is carried out in the absence of any solvents; and
   wherein, according to synthesis route (B), the reaction is carried out autocatalytically or in the presence of a catalyst; and
   wherein, according to synthesis route (B), the compound of general formula (Ib) and the fatty alcohol (II) are used in a molar ratio of compound of the general formula (Ib)/fatty alcohol (II) in a range of from 1:1 to 10:1.

5. The method according to claim 1,
   wherein, according to synthesis route (B), the hydrolysis of the acyl group is carried out in the presence of an enzyme as a catalyst;
   wherein the enzyme is selected from synthetases (ligases), catalases, esterases, lipases and combinations thereof; and
   wherein the enzyme is used in immobilized form on a carrier; and
   wherein the enzyme is used in amounts, based on the total amount of the compound to be hydrolyzed, in the range of from 0.001% by weight to 20% by weight; and
   wherein the enzyme is recycled after the hydrolysis reaction.

6. The method according to claim 1,
   wherein the fatty alcohol (II) corresponds to the general formula (II')

$$R^3-OH \quad (II')$$

wherein the radical $R^3$ represents a linear or branched, saturated or mono- or polyunsaturated aliphatic $C_{10}$-$C_{30}$-alkyl radical.

7. The method according to claim 6,
   wherein the radical $R^3$ represents a 1-decanyl radical, a 1-dodecanyl radical, a 1-tetradecanyl radical, a 1-hexadecanyl radical, a 1-heptadecanyl radical, a 1-octadecanyl radical, a 1-eicosanyl radical, a 1-docosanyl radical, a 1-tetracosanyl radical, a 1-hexacosanyl radical, a 1-octacosanyl radical, a 1-tricontanyl radical, a cis-9-hexadecen-1-yl radical, a cis-9-octadecen-1-yl radical, a trans-9-octadecen-1-yl radical, a cis-11-octadecen-1-yl radical, a cis, cis-9,12-octadecadien-1-yl radical or a 6,9,12-octadecatrien-1-yl radical.

8. The method according to according to claim 1,
   wherein the fatty alcohol (II) is selected from linear, saturated or mono- or polyunsaturated, aliphatic monohydric and primary $C_{10}$-$C_{30}$-fatty alcohols; and
   wherein the fatty alcohol (II) is selected from the group of 1-decanol, 1-dodecanol, 1-tetradecanol, 1-hexadecanol, 1-heptadecanol, 1-octadecanol, 1-eicosanol, 1-docosanol, 1-tetracosanol, 1-hexacosanol, 1-octacosanol, 1-tricontanol, cis-9-hexadecen-1-ol, cis-9-octadecen-1-ol, trans-9-octadecen-1-ol, cis-11-octadecen-1-ol, cis, cis-9,12-octadecadien-1-ol, 6,9,12-octadecatrien-1-ol and combinations thereof.

9. A fatty alcohol ester of acylated 3-hydroxybutyric acid, wherein the fatty alcohol ester of acylated 3-hydroxybutyric acid is a fatty alcohol ester of acylated 3-hydroxybutyric acid of the general formula (IIIa)

$$CH_3—CH(OR^2)—CH_2—C(O)OR^3 \qquad (IIIa)$$

wherein, in the general formula (IIIa),
R² represents an acyl group selected from an acetyl group of formula —C(O)—CH₃ and a propionyl group of formula —C(O)—C₂H₅,
the radical R³ represents a 1-decanyl radical, a 1-dodecanyl radical, a 1-tetradecanyl radical, a 1-hexadecanyl radical, a 1-heptadecanyl radical, a 1-octadecanyl radical, a 1-eicosanyl radical, a 1-docosanyl radical, a 1-tetracosanyl radical, a 1-hexacosanyl radical, a 1-octacosanyl radical, a 1-tricontanyl radical, a cis-9-hexadecen-1-yl radical, a cis-9-octadecen-1-yl radical, a trans-9-octadecen-1-yl radical, a cis-11-octadecen-1-yl radical, a cis, cis-9,12-octadecadien-1-yl radical or a 6,9,12-octadecatrien-1-yl radical.

10. A pharmaceutical composition,
wherein the pharmaceutical composition comprises at least one of (i) and (ii):
(i) a fatty alcohol ester of 3-hydroxybutyric acid, wherein the fatty alcohol ester of 3-hydroxybutyric acid corresponds to the general formula (III')

$$CH_3—CH(OH)—CH_2—C(O)OR^3 \qquad (III')$$

wherein the radical R³ represents a 1-tetradecanyl radical, a 1-hexadecanyl radical, a 1-heptadecanyl radical, a 1-octadecanyl radical, a 1-eicosanyl radical, a 1-docosanyl radical, a 1-tetracosanyl radical, a 1-tricontanyl radical, a cis-9-hexadecen-1-yl radical, a cis-9-octadecen-1-yl radical, a trans-9-octadecen-1-yl radical, a cis-11-octadecen-1-yl radical, a cis, cis-9,12-octadecadien-1-yl radical or a 6,9,12-octadecatrien-1-yl radical;
(ii) a fatty alcohol ester of acylated 3-hydroxybutyric acid, wherein the fatty alcohol ester of acylated 3-hydroxybutyric acid is a fatty alcohol ester of acylated 3-hydroxybutyric acid of the general formula (IIIa)

$$CH_3—CH(OR^2)—CH_2—C(O)OR^3 \qquad (IIIa)$$

wherein, in the general formula (IIIa),
R² represents an acyl group selected from an acetyl group of formula —C(O)—CH₃ and a propionyl group of formula —C(O)—C₂H₅,
the radical R³ represents a 1-decanyl radical, a 1-dodecanyl radical, a 1-tetradecanyl radical, a 1-hexadecanyl radical, a 1-heptadecanyl radical, a 1-octadecanyl radical, a 1-eicosanyl radical, a 1-docosanyl radical, a 1-tetracosanyl radical, a 1-hexacosanyl radical, a 1-octacosanyl radical, a 1-tricontanyl radical, a cis-9-hexadecen-1-yl radical, a cis-9-octadecen-1-yl radical, a trans-9-octadecen-1-yl radical, a cis-11-octadecen-1-yl radical, a cis, cis-9,12-octadecadien-1-yl radical or a 6,9,12-octadecatrien-1-yl radical.

11. The pharmaceutical composition according to claim 10,
wherein the pharmaceutical composition is a drug or medicament.

12. A method of treating a human suffering from a disease, wherein the method comprises a step of administering to said human an efficient dose of a pharmaceutical composition, wherein the pharmaceutical composition comprises at least one of (i) and (ii):
(i) a fatty alcohol ester of 3-hydroxybutyric acid, wherein the fatty alcohol ester of 3-hydroxybutyric acid corresponds to the general formula (III')

$$CH_3—CH(OH)—CH_2—C(O)OR^3 \qquad (III')$$

wherein the radical R³ represents a 1-tetradecanyl radical, a 1-hexadecanyl radical, a 1-heptadecanyl radical, a 1-octadecanyl radical, a 1-eicosanyl radical, a 1-docosanyl radical, a 1-tetracosanyl radical, a 1-tricontanyl radical, a cis-9-hexadecen-1-yl radical, a cis-9-octadecen-1-yl radical, a trans-9-octadecen-1-yl radical, a cis-11-octadecen-1-yl radical, a cis, cis-9,12-octadecadien-1-yl radical or a 6,9,12-octadecatrien-1-yl radical;
(ii) a fatty alcohol ester of acylated 3-hydroxybutyric acid, wherein the fatty alcohol ester of acylated 3-hydroxybutyric acid is a fatty alcohol ester of acylated 3-hydroxybutyric acid of the general formula (IIIa)

$$CH_3—CH(OR^2)—CH_2—C(O)OR^3 \qquad (IIIa)$$

wherein, in the general formula (IIIa),
R² represents an acyl group selected from an acetyl group of formula —C(O)—CH₃ and a propionyl group of formula —C(O)—C₂H₅,
the radical R³ represents a 1-decanyl radical, a 1-dodecanyl radical, a 1-tetradecanyl radical, a 1-hexadecanyl radical, a 1-heptadecanyl radical, a 1-octadecanyl radical, a 1-eicosanyl radical, a 1-docosanyl radical, a 1-tetracosanyl radical, a 1-hexacosanyl radical, a 1-octacosanyl radical, a 1-tricontanyl radical, a cis-9-hexadecen-1-yl radical, a cis-9-octadecen-1-yl radical, a trans-9-octadecen-1-yl radical, a cis-11-octadecen-1-yl radical, a cis, cis-9,12-octadecadien-1-yl radical or a 6,9,12-octadecatrien-1-yl radical.

13. The method according to claim 12,
wherein the disease is selected from the group consisting of diseases associated with a disorder of the energy metabolism, diseases associated with a keto-body metabolism, craniocerebral trauma, stroke, hypoxia, cardiovascular diseases, myocardial infarction, refeeding syndrome, anorexia, epilepsy, neurodegenerative diseases, dementia, Alzheimer's disease, Parkinson's disease, multiple sclerosis, amyotrophic lateral sclerosis, fat metabolic diseases, glucose transporter defect (GLUT1 defect), VL-FAOD and mitochondriopathies, mitochondrial thiolase defect, Huntington's disease, cancers, T-cell lymphomas, astrocytomas and glioblastomas, HIV, rheumatic diseases, rheumatoid arthritis and arthritis urica, diseases of the gastrointestinal tract, chronic inflammatory bowel diseases, ulcerative colitis and Crohn's disease, lyosomal storage diseases, sphingolipidosis, Niemann-Pick disease, diabetes mellitus and effects or side-effects of chemotherapy.

14. A food product,
wherein the food product comprises at least one of (i) and (ii):
(i) a fatty alcohol ester of 3-hydroxybutyric acid, wherein the fatty alcohol ester of 3-hydroxybutyric acid corresponds to the general formula (III')

$$CH_3—CH(OH)—CH_2—C(O)OR^3 \qquad (III')$$

wherein the radical R³ represents a 1-tetradecanyl radical, a 1-hexadecanyl radical, a 1-heptadecanyl radical, a 1-octadecanyl radical, a 1-eicosanyl radical, a 1-docosanyl radical, a 1-tetracosanyl radical, a 1-tricontanyl radical, a cis-9-hexadecen-1-yl radical, a cis-9-octadecen-1-yl radical, a trans-9-octadecen-1-yl radical, a cis-11-octadecen-1-yl radical, a cis, cis-9,12-octadecadien-1-yl radical or a 6,9,12-octadecatrien-1-yl radical;

(ii) a fatty alcohol ester of acylated 3-hydroxybutyric acid, wherein the fatty alcohol ester of acylated 3-hydroxybutyric acid is a fatty alcohol ester of acylated 3-hydroxybutyric acid of the general formula (IIIa)

$$CH_3-CH(OR^2)-CH_2-C(O)OR^3 \qquad (IIIa)$$

wherein, in the general formula (IIIa), $R^2$ represents an acyl group selected from an acetyl group of formula $-C(O)-CH_3$ and a propionyl group of formula $-C(O)-C_2H_5$, the radical $R^3$ represents a 1-decanyl radical, a 1-dodecanyl radical, a 1-tetradecanyl radical, a 1-hexadecanyl radical, a 1-heptadecanyl radical, a 1-octadecanyl radical, a 1-eicosanyl radical, a 1-docosanyl radical, a 1-tetracosanyl radical, a 1-hexacosanyl radical, a 1-octacosanyl radical, a 1-tricontanyl radical, a cis-9-hexadecen-1-yl radical, a cis-9-octadecen-1-yl radical, a trans-9-octadecen-1-yl radical, a cis-11-octadecen-1-yl radical, a cis, cis-9,12-octadecadien-1-yl radical or a 6,9,12-octadecatrien-1-yl radical.

* * * * *